United States Patent
Abe et al.

(10) Patent No.: US 9,130,173 B2
(45) Date of Patent: Sep. 8, 2015

(54) QUINOLINO[3,2,1-KL]PHENOXAZINE COMPOUND AND ORGANIC LIGHT EMITTING ELEMENT USING THE SAME

(75) Inventors: Shigemoto Abe, Yokohama (JP); Tetsuya Kosuge, Yokohama (JP); Jun Kamatani, Tokyo (JP); Kengo Kishino, Tokyo (JP)

(73) Assignee: Canon Kabushiki Kaisha, Tokyo (JP)

(*) Notice: Subject to any disclaimer, the term of this patent is extended or adjusted under 35 U.S.C. 154(b) by 0 days.

(21) Appl. No.: 13/885,124

(22) PCT Filed: Nov. 8, 2011

(86) PCT No.: PCT/JP2011/076128
§ 371 (c)(1),
(2), (4) Date: May 13, 2013

(87) PCT Pub. No.: WO2012/073679
PCT Pub. Date: Jun. 7, 2012

(65) Prior Publication Data
US 2013/0228768 A1 Sep. 5, 2013

(30) Foreign Application Priority Data
Dec. 1, 2010 (JP) ................................ 2010-268480

(51) Int. Cl.
*H01L 29/08* (2006.01)
*H01L 31/062* (2012.01)
(Continued)

(52) U.S. Cl.
CPC .......... *H01L 51/0071* (2013.01); *C07D 519/00* (2013.01); *H01L 51/0059* (2013.01);
(Continued)

(58) Field of Classification Search
CPC ............ H01L 51/0054; H01L 51/0059; H01L 51/0067; H01L 51/0072; H01L 51/5203; H01L 51/0085; H01L 51/5056; H01L 51/0071; H01L 51/0074; H01L 2251/5338; H05B 33/20; C07D 519/00
USPC .................. 257/40; 544/73, 14, 1, 3
See application file for complete search history.

(56) References Cited

U.S. PATENT DOCUMENTS 3,337,545 A 8/1967 Zirkle
(Continued)

FOREIGN PATENT DOCUMENTS

JP H05-107784 A 4/1993
(Continued)

OTHER PUBLICATIONS

U.S. Appl. No. 13/885,883, filed May 16, 2013.
(Continued)

*Primary Examiner* — Chuong A Luu
*Assistant Examiner* — Moazzam Hossain
(74) *Attorney, Agent, or Firm* — Fitzpatrick, Cella, Harper & Scinto

(57) ABSTRACT

Provided is an excellent organic light emitting element having high emission efficiency and a low drive voltage. The organic light emitting element includes an anode, a cathode, and an organic compound layer disposed between the anode and the cathode, in which the organic compound layer includes a quinolino[3,2,1-kl]phenoxazine compound represented by the following general formula [1]:

[1]

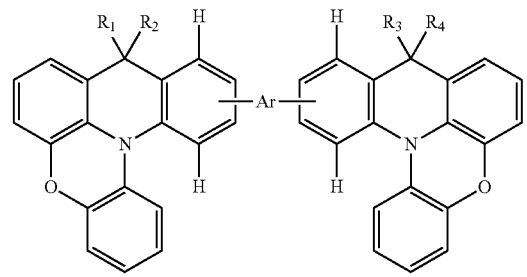

where $R_1$ to $R_4$ each represent a hydrogen atom or an alkyl group having 1 to 3 carbon atoms, $R_1$ to $R_4$ may be identical to or different from each other, and Ar represents a single bond or an oligophenylene group having 6 to 18 carbon atoms.

12 Claims, 1 Drawing Sheet

(51) Int. Cl.
*H01L 51/00* (2006.01)
*C07D 519/00* (2006.01)
*H05B 33/20* (2006.01)
*H01L 51/52* (2006.01)
*H01L 51/50* (2006.01)

(52) U.S. Cl.
CPC ............ *H01L51/5203* (2013.01); *H05B 33/20* (2013.01); *H01L 51/0054* (2013.01); *H01L 51/0067* (2013.01); *H01L 51/0072* (2013.01); *H01L 51/0074* (2013.01); *H01L 51/0085* (2013.01); *H01L 51/5056* (2013.01); *H01L 2251/5338* (2013.01)

(56) References Cited

U.S. PATENT DOCUMENTS

| | | | |
|---|---|---|---|
| 7,883,786 | B2 | 2/2011 | Abe et al. |
| 7,923,129 | B2 | 4/2011 | Igawa et al. |
| 8,110,824 | B2 | 2/2012 | Yamada et al. |
| 8,293,383 | B2 | 10/2012 | Horiuchi et al. |
| 2006/0289535 | A1* | 12/2006 | Sung et al. .................. 219/761 |
| 2007/0232803 | A1 | 10/2007 | Kamatani et al. |
| 2011/0024737 | A1 | 2/2011 | Horiuchi et al. |

FOREIGN PATENT DOCUMENTS

| | | |
|---|---|---|
| WO | 2004/093207 A2 | 10/2004 |
| WO | 2009/021126 A2 | 2/2009 |
| WO | 2009/139501 A | 11/2009 |
| WO | 2010/050778 A1 | 5/2010 |
| WO | 2011/107186 A | 9/2011 |

OTHER PUBLICATIONS

H. Dieter et al., "Modified Tetrahelicene Systems. III. Doubly Ortho-bridged Triphenylamine Derivatives", Chemische Berichte, vol. 113, pp. 358-384 (1980).

K. Dedeian et al., "A New Synthetic Route to the Preparation of a Series of Strong Photoreducing Agents: fac Tris-Ortho-Metalated Complexes of Iridium (III) with Substituted 2-Phenylpyridines", Inorganic Chemistry, vol. 30, No. 9, p. 1685-1687 (1991).

S. Tokito et al., "Confinement of Triplet Energy on Phosphorescent Molecules for Highly-efficient Organic Blue-Light Emitting Devices", Applied Physics Letters, vol. 83, No. 3, p. 569-571 (2003).

Extended European Search Report issued in counterpart application No. 11844468.6 dated Apr. 9, 2014—4 pages.

* cited by examiner

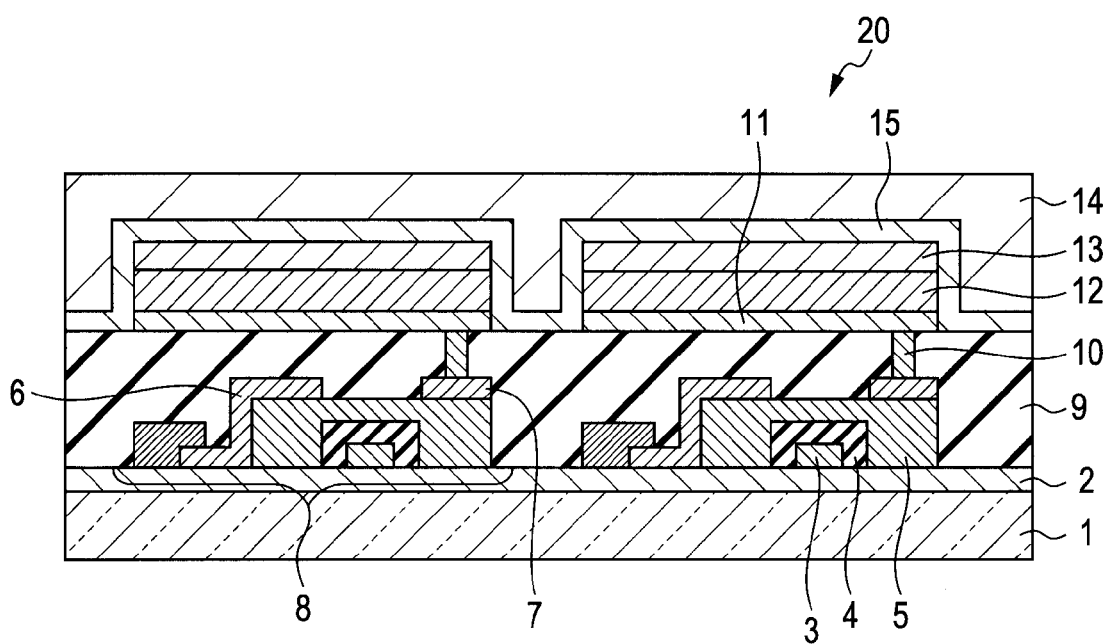

QUINOLINO[3,2,1-KL]PHENOXAZINE COMPOUND AND ORGANIC LIGHT EMITTING ELEMENT USING THE SAME

TECHNICAL FIELD

The present invention relates to a quinolino[3,2,1-kl]phenoxazine compound and an organic light emitting element using the same.

BACKGROUND ART

An organic light emitting element is an electronic element including an anode, a cathode, and an organic compound layer disposed between both the electrodes. Holes and electrons to be injected from the respective electrodes recombine with each other in the organic compound layer (in particular, emission layer). When excitons generated by the recombination return to the ground state, the organic light emitting element emits light.

Recent advances in the organic light emitting element are remarkable, and have resulted in the following features, for example. That is, the organic light emitting element has a low drive volatage, a variety of emission wavelengths, and high-speed responsiveness, and allows a light emitting device to be reduced in thickness and weight.

Meanwhile, the organic light emitting element is broadly classified into a fluorescent light emitting element and a phosphorescent light emitting element depending on the kind of excitons involved in emission. In particular, the phosphorescent light emitting element is an electronic element including a phosphorescent light emitting material in an organic compound layer, specifically an emission layer, which constructs the organic light emitting element, in which triplet excitons are involved in emission. Here, the phosphorescent light emitting material is excited to the triplet state through the recombination of holes and electrons, and emits phosphorescent light when returning to the ground state. Thus, the phosphorescent light emitting element is an organic light emitting element which provides emission derived from the triplet excitons.

Further, the phosphorescent light emitting element has attracted attention in recent years because the internal quantum efficiency of the phosphorescent light emitting element is four times as large as the internal quantum efficiency of the fluorescent light emitting element in theory. However, in the phosphorescent light emitting element, there is a room for further improvement in emission efficiency.

Meanwhile, there are various proposals concerning materials to be used in the phosphorescent light emitting element. For example, there are proposals concerning the following compounds GH-01 and GH-02 (see International Publication WO2010/050778).

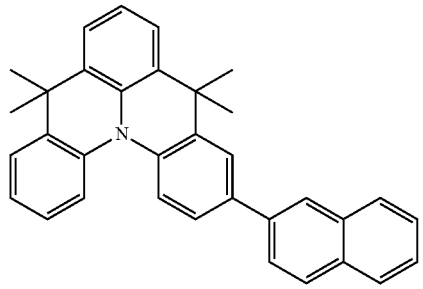

GH-01

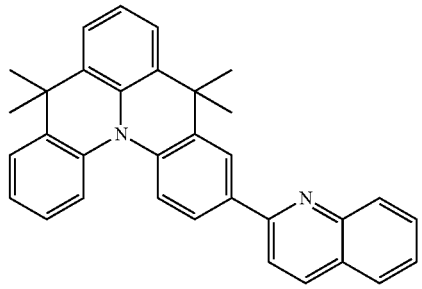

GH-02

On the other hand, there is known quinolino[3,2,1-kl]phenoxazine as a compound having a structure similar to those of the above-mentioned compounds GH-01 and GH-02. Modified tetrahelicene systems. III. Doubly ortho-bridged triphenylamine derivatives (Hellwinkel, Dieter et al., Chemische Berichte, Vol. 113, p. 358 (1980)) discloses a synthesis method therefor.

SUMMARY OF INVENTION

However, the compounds proposed in International Publication WO2010/050778 do not simultaneously satisfy high durability, high lowest triplet excited state energy ($T_1$ energy), and a shallow HOMO level (small ionization potential energy). Further, Modified tetrahelicene systems. III. Doubly ortho-bridged triphenylamine derivatives (Hellwinkel, Dieter et al., Chemische Berichte, Vol. 113, p. 358 (1980)) fails to propose any application of the compounds disclosed therein to an organic light emitting element.

The present invention has been made in order to solve the above-mentioned problems. An object of the present invention is to provide an excellent organic light emitting element having high emission efficiency and a low drive volatage.

A quinolino[3,2,1-kl]phenoxazine compound of the present invention is represented by the following general formula [1]:

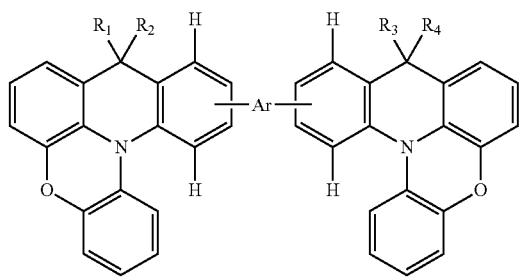

[1]

where $R_1$ to $R_4$ each represent a hydrogen atom or an alkyl group having 1 to 3 carbon atoms, $R_1$ to $R_4$ may be identical to or different from each other, and Ar represents a single bond or an oligophenylene group having 6 to 18 carbon atoms.

The quinolino[3,2,1-kl]phenoxazine compound of the present invention is a compound which is hard to deteriorate and has high $T_1$ energy and a shallow HOMO level. Thus, according to the present invention, it is possible to provide the organic light emitting element having high emission efficiency and a low drive volatage.

Further features of the present invention will become apparent from the following description of exemplary embodiments with reference to the attached drawings.

BRIEF DESCRIPTION OF DRAWING

FIG. 1 is a cross-sectional schematic diagram illustrating an example of a display device including an organic light emitting element of the present invention and a TFT element as an example of a switching element connected to the organic light emitting element.

DESCRIPTION OF EMBODIMENTS

Preferred embodiments of the present invention will now be described in detail in accordance with the accompanying drawings.

A quinolino[3,2,1-kl]phenoxazine compound of the present invention is described. The quinolino[3,2,1-kl]phenoxazine compound of the present invention is a compound represented by the following general formula [1].

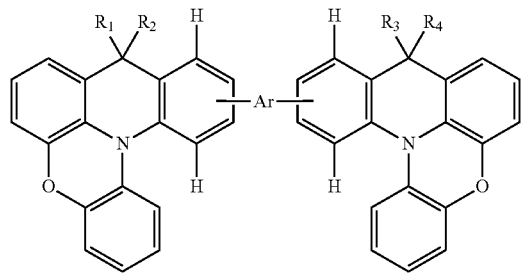

[1]

In the formula [1], $R_1$ to $R_4$ each represent a hydrogen atom or an alkyl group having 1 to 3 carbon atoms.

Examples of the alkyl group represented by each of $R_1$ to $R_4$ include a methyl group, an ethyl group, an n-propyl group, and an iso-propyl group.

$R_1$ to $R_4$ may be identical to or different from each other.

In the formula [1], Ar represents a single bond or an oligophenylene group having 6 to 18 carbon atoms. It should be noted that details of the oligophenylene group (having 6 to 18 carbon atoms) represented by Ar are described later.

The quinolino[3,2,1-kl]phenoxazine compound of the present invention is preferably a compound represented by the following formula [2].

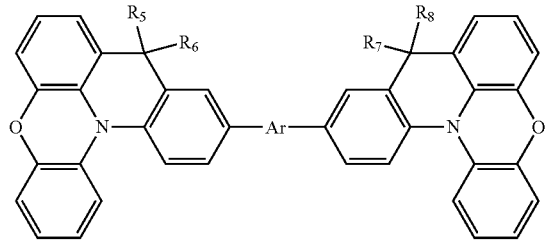

[2]

In the formula [2], $R_5$ to $R_8$ each represent a hydrogen atom or an alkyl group having 1 to 3 carbon atoms.

Examples of the alkyl group represented by each of $R_5$ to $R_8$ include a methyl group, an ethyl group, an n-propyl group, and an iso-propyl group.

$R_5$ to $R_8$ may be identical to or different from each other.

In the formula [2], Ar represents a single bond or an oligophenylene group having 6 to 18 carbon atoms. It should be noted that Ar in the formula [2] is the same as Ar in the formula [1].

Here, the oligophenylene group (having 6 to 18 carbon atoms) represented by Ar in each of the formulae [1] and [2] refers to the following substituent (i) or (ii).

(i) Divalent substituent formed of one benzene ring (ii) Divalent substituent formed of two or three benzene rings linked together in a meta or para orientation The oligophenylene group represented by Ar is preferably a substituent represented by the following general formula [3].

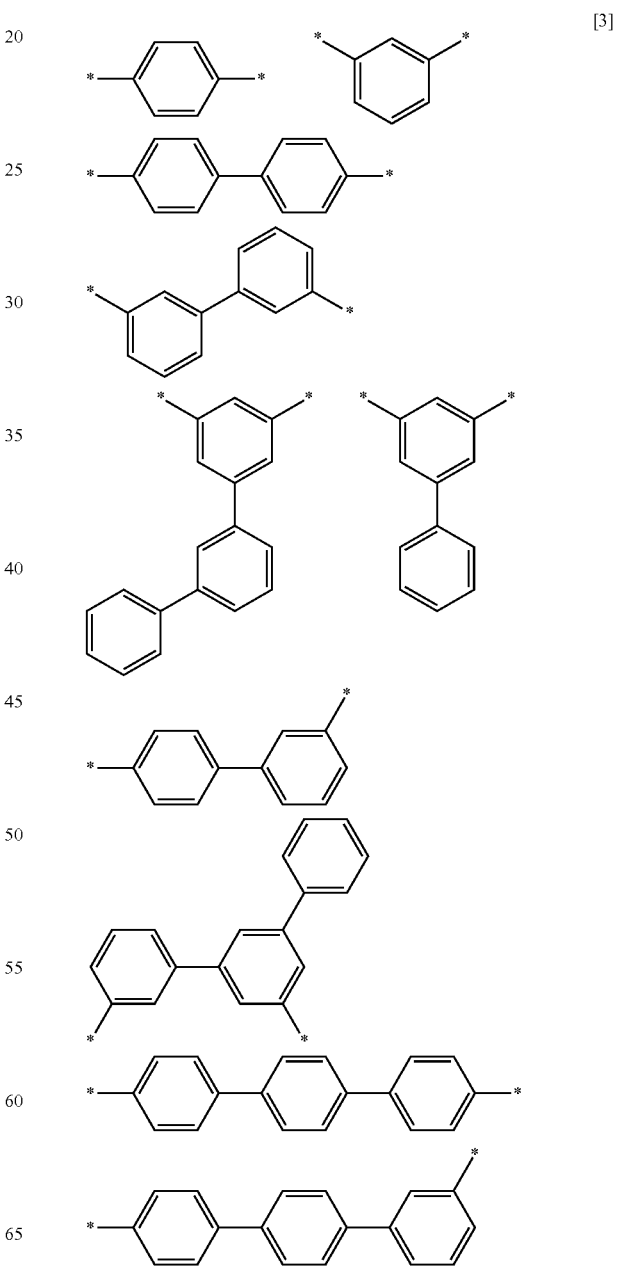

[3]

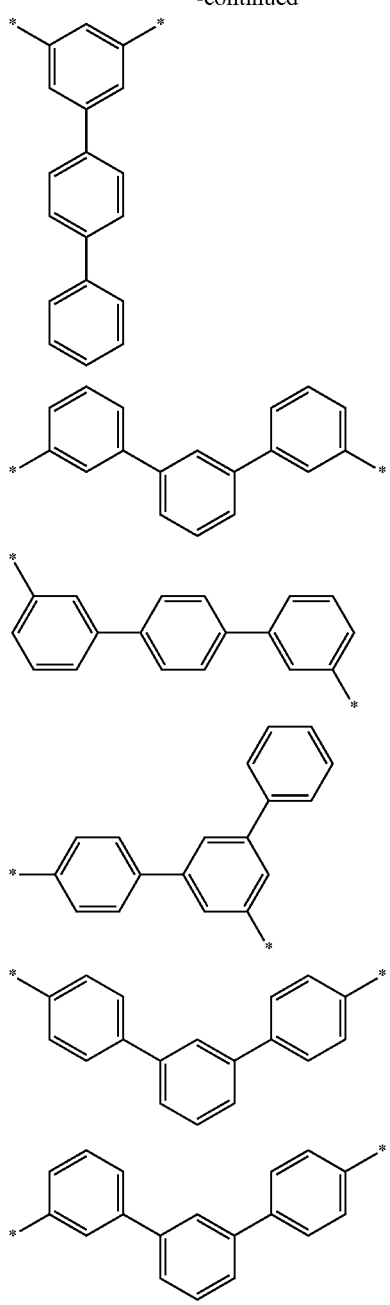

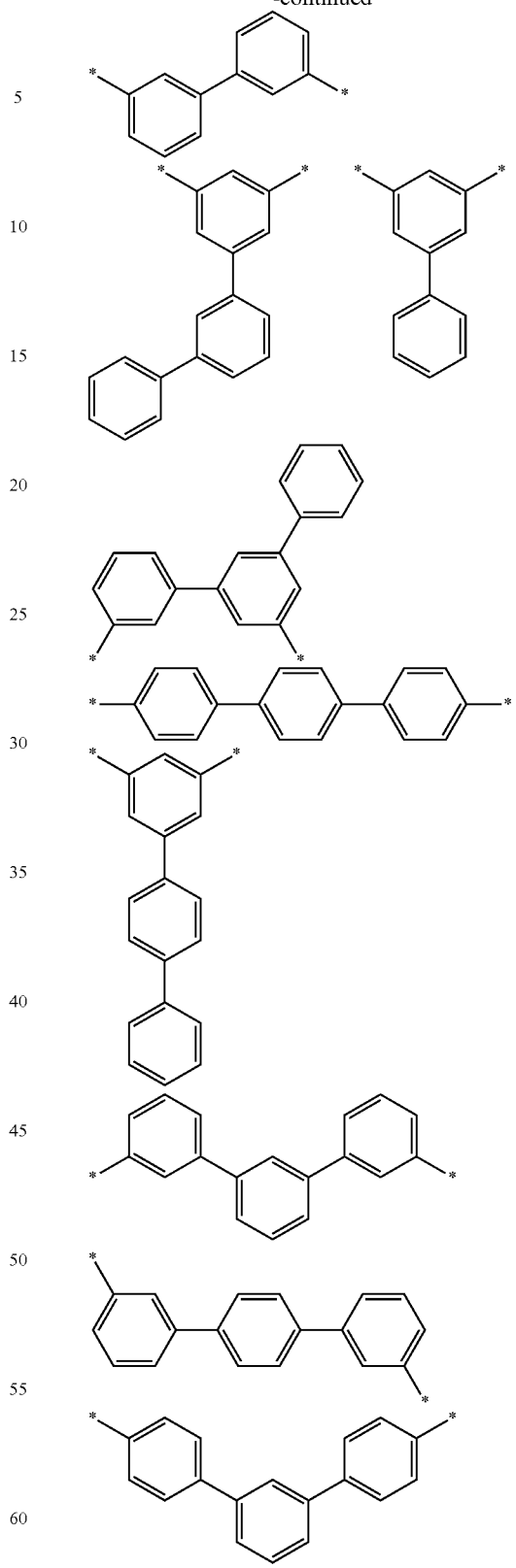

In the formula [3], * represents a position at which the oligophenylene group is bonded to quinolino[3,2,1-kl]phenoxazine in the formula [2].

The substituent represented by the formula [3] is preferably the following substituent.

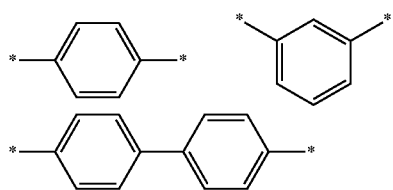

Next, a synthesis method for the quinolino[3,2,1-kl]phenoxazine compound of the present invention is described.

In the synthesis of the quinolino[3,2,1-kl]phenoxazine compound of the present invention, first, as represented by the following formula [4], a quinolino[3,2,1-kl]phenoxazine bispinacol boronic acid ester or boronic acid compound is synthesized. It should be noted that, in the formula [4], $R_9$ represents the same substituent as those for $R_1$ in the formula [1] and $R_5$ in the formula [2], i.e., an alkyl group having 1 to 3 carbon atoms.

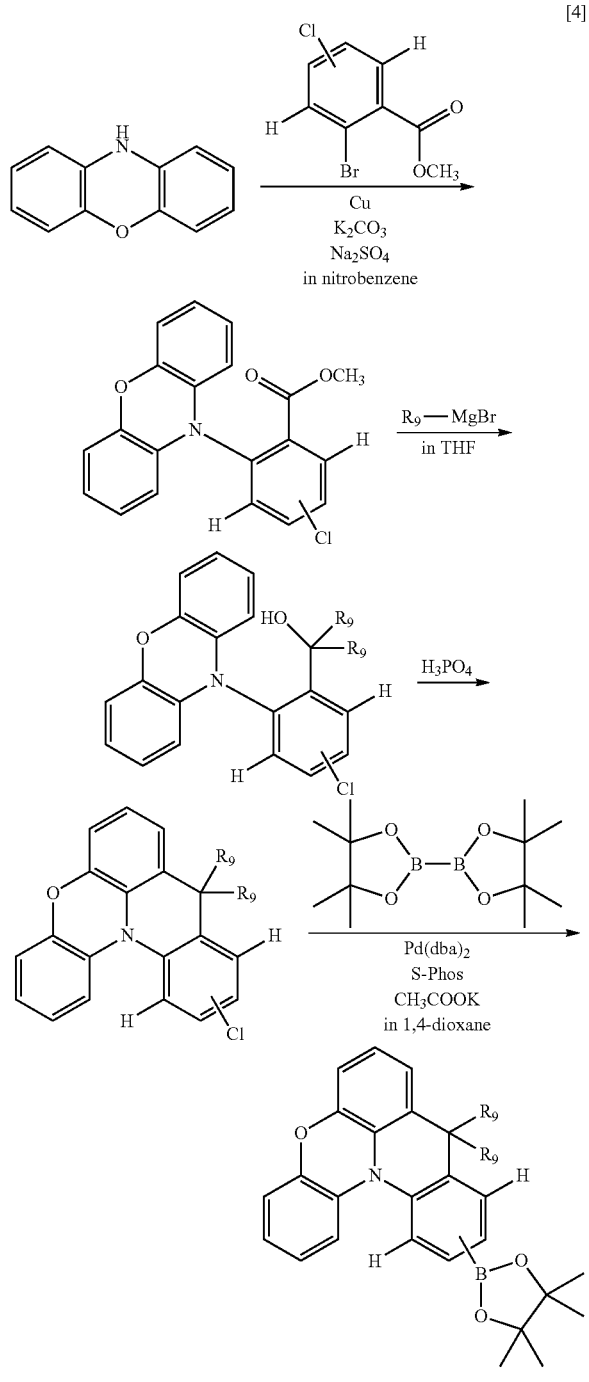

However, a synthesis scheme of the formula [4] is merely a specific example, and the present invention is by no means limited thereto. It should be noted that, when an LAH reagent is used in place of a Grignard reagent in a reaction at the second stage of the synthesis scheme of the formula [4], a quinolino[3,2,1-kl]phenoxazine compound, in which $R_1$ to $R_4$ in the formula [1] and $R_5$ to $R_8$ in the formula [2] each represent a hydrogen atom, may be synthesized.

Meanwhile, a dihalogenobenzoic acid ester is used in the formula [4]. Here, in order to couple phenoxazine with the dihalogenobenzoic acid ester at a predetermined position, it is preferred that two halogen atoms possessed by (the benzene ring of) the dihalogenobenzoic acid ester be different from each other. Specifically, it is preferred that a halogen atom at a position at which phenoxazine is coupled with the dihalogenobenzoic acid ester be made heavier than the other halogen atom.

Further, when the dihalogenobenzoic acid ester is used, as represented by the formula [4], $R_1$ and $R_2$ in the formula [1] ($R_5$ and $R_6$ in the formula [2]) each represent the same substituent ($R_9$). Here, when the following compound is used in place of the dihalogenobenzoic acid ester, a compound, in which $R_1$ and $R_2$ in the formula [1] ($R_5$ and $R_6$ in the formula [2]) represent substituents different from each other, may be synthesized.

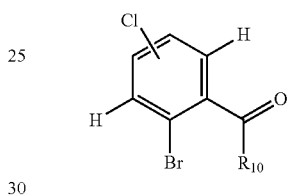

($R_{10}$ represents a hydrogen atom or an alkyl group having 1 to 3 carbon atoms. It should be noted that $R_{10}$ may be identical to or different from $R_9$ in the formula [4].)

Next, for example, as represented by the following formula [5] or [6], a quinolino[3,2,1-kl]phenoxazine boronic acid compound is coupled with dihalogenated Ar or halogenated quinolino[3,2,1-kl]phenoxazine using a Pd catalyst. Thus, the quinolino[3,2,1-kl]phenoxazine compound of the present invention may be synthesized.

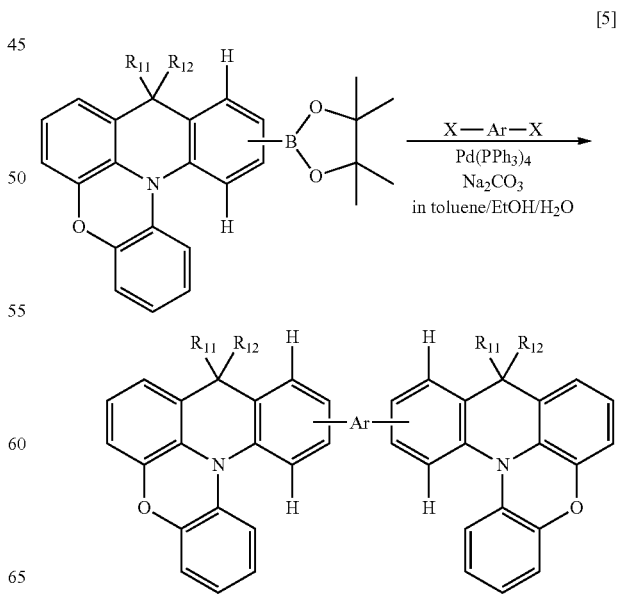

-continued

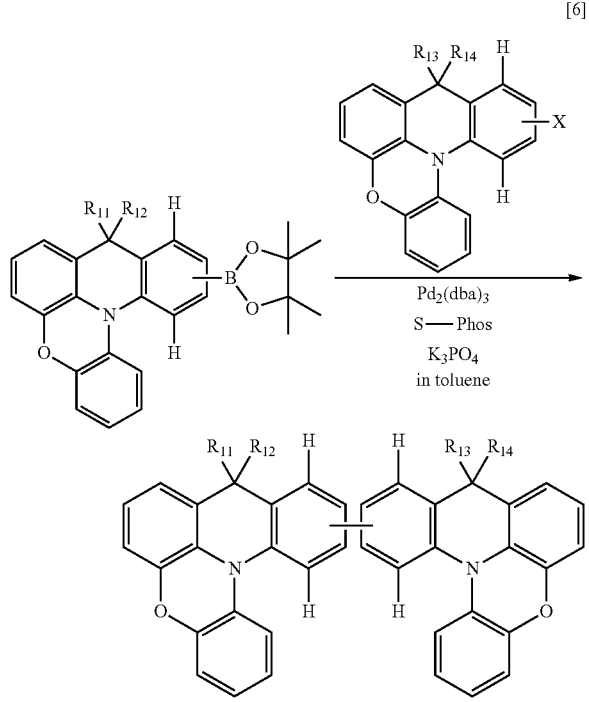

(In the formula [5], $R_{11}$ to $R_{14}$ each represent a hydrogen atom or an alkyl group having 1 to 3 carbon atoms and may be identical to or different from each other, Ar represents an oligophenylene group having 6 to 18 carbon atoms, and X represents chlorine, bromine, or iodine. In the formula [6], $R_{11}$ to $R_{14}$ each represent a hydrogen atom or an alkyl group having 1 to 3 carbon atoms and may be identical to or different from each other, and X represents chlorine, bromine, or iodine.)

However, in the event of the following case (A) or (B), it is preferred that halogen atoms of dihalogenated Ar be different from each other from the synthetic viewpoint.

(A) Case where the following quinolino[3,2,1-kl]phenoxazine ring has one bond at the 11-position and the other bond at the 12-position

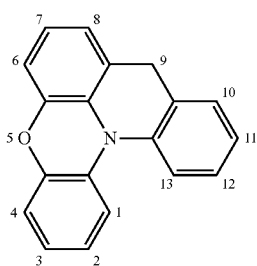

(B) Case where different kinds of quinolino[3,2,1-kl]phenoxazine rings are linked together via an oligophenylene group It should be noted that any of quinolino[3,2,1-kl]phenoxazine bispinacol boronic acid ester compounds may be first coupled with a dihalogenated oligophenylene.

A desired quinolino[3,2,1-kl]phenoxazine compound according to the present invention may be synthesized by appropriately selecting Ar in the above-mentioned reaction.

Further, when the quinolino[3,2,1-kl]phenoxazine compound of the present invention is used as a material for constructing an organic light emitting element, the compound is preferably subjected to sublimation purification immediately before use. This is because sublimation purification provides a large purification effect in enhancing the purity of an organic compound. Here, in general, a compound having a larger molecular weight needs to be subjected to sublimation purification at a higher temperature. Further, an organic compound to be purified is more liable to undergo heat decomposition and the like at a higher temperature. Accordingly, it is preferred that the organic compound to be used as a material for constructing an organic light emitting element have a molecular weight of 1,000 or less so that the organic compound may be subjected to sublimation purification without being excessively heated.

Next, characteristics of the quinolino[3,2,1-kl]phenoxazine compound of the present invention are described. In the quinolino[3,2,1-kl]phenoxazine compound of the present invention, two quinolino[3,2,1-kl]phenoxazine rings are linked together at the 11-position or the 12-position directly or via an oligophenylene group having 6 to 18 carbon atoms. Here, substitution position numbers of a quinolino[3,2,1-kl]phenoxazine ring are shown below.

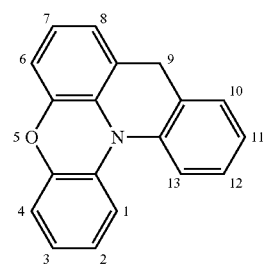 [SMILES: c1ccc2c(c1)Cc1cccc3c1N2c1ccccc1O3]

Meanwhile, quinolino[3,2,1-kl]phenoxazine has a feature in a small difference between lowest triplet excited state energy ($T_1$ energy) and lowest singlet excited state energy ($S_1$ energy). Thus, the use thereof as a material for constructing a phosphorescent light emitting element can be expected to reduce the drive volatage of the element.

Further, quinolino[3,2,1-kl]phenoxazine has a structure in which three benzene rings which construct a triphenylamine skeleton are cross-linked together at two positions via an oxygen atom or a methylene group. Such structure provides the following two improvements over triphenylamine.

One of the improvements is an improvement in bonding property between an N atom and a benzene ring. In triphenylamine, positions at which an N atom constructing the amine is bonded to phenyl groups (benzene rings) each have the lowest bond energy. That is, bonds (C—N bonds) between the N atom constructing the amine and C atoms in the phenyl groups are liable to be cleaved. Further, once the C—N bonds are cleaved for the reason of excitation or the like, the amine dissociates from the phenyl groups in a system, which makes it difficult to form a triphenylamine structure again. However, in the quinolino[3,2,1-kl]phenoxazine compound of the present invention, even when one of three bonds (C—N bonds) between the amine and the three phenyl groups is cleaved, the phenyl groups are cross-linked together via an oxygen atom (ether bond) or a methylene group. Thus, even after the cleavage of a C—N bond, the separated amine and phenyl group are present adjacent to each other. Thus, the amine and the phenyl group are more likely to recombine with each other. Accordingly, the use of the quinolino[3,2,1-kl]phenoxazine compound of the present invention as a material for constructing an organic light emitting element improves a problem of a degradation in element life due to excitation deterioration of the material.

Further, in the organic light emitting element, a large amount of holes are injected from an anode in a hole transport layer. Hence, a material for constructing the hole transport layer is preferably a material which is resistant to the repetition of a cationic state and a neutral state. As one method of increasing the resistance to the repetition of the cationic state and the neutral state, it is desirable to select a material which is relatively stable in a cationic state. This is because, when the cationic state is unstable, a chemical reaction in which a compound changes into another compound is liable to occur rescent material Ir(ppy)$_3$ (guest), the host to be used preferably has an HOMO level of about 5.6 eV. It should be noted that Ir(ppy)$_3$ as the guest also has an HOMO level of about 5.6 eV.

Further, as described above, in quinolino[3,2,1-kl]phenoxazine, the amine can supply electrons through an oxygen atom (ether bond) or a methylene group for cross-linking phenyl groups together. Thus, out of amine-containing heterocycles, the amine has a feature of having a particularly shallow HOMO level. Table 1 below is a table showing HOMO levels of compounds each having a triphenylamine skeleton including quinolino[3,2,1-kl]phenoxazine. It should be noted that the HOMO levels shown in Table 1 are calculated values obtained by molecular orbital calculation.

TABLE 1

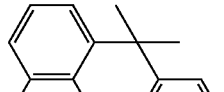

| Structural formula | | | | |
| --- | --- | --- | --- | --- |
| HOMO level (Calculated value) | −4.80 eV | −4.95 eV | −4.93 eV | −4.84 eV | in the cationic state. Here, in the quinolino[3,2,1-kl]phenoxazine compound of the present invention, an oxygen atom (ether bond) and a methylene group, each of which cross-links together three phenyl groups constructing a triphenylamine skeleton, are both present at positions suitable for the donation of electrons to an amine. Therefore, even when the compound itself turns into the cationic state, electrons are donated from the oxygen atom (ether bond) or the methylene group toward (the N atom constructing) the amine. Thus, the quinolino[3,2,1-kl]phenoxazine compound of the present invention allows an aminium cation radical to exist stably as compared to the case of triphenylamine. Accordingly, the compound becomes resistant to the repetition of the cationic state and the neutral state. Thus, the use of the quinolino[3,2,1-kl]phenoxazine compound of the present invention as the material for constructing the organic light emitting element improves a problem of a degradation in element life due to deterioration of the material caused by a combination with holes.

The other of the improvements with quinolino[3,2,1-kl]phenoxazine is an improvement in HOMO level.

Meanwhile, when holes are injected from a hole transport layer toward an emission layer in an organic light emitting element, a smaller difference in HOMO level at the interface between the hole transport layer and the emission layer leads to a smaller voltage at which the element is driven. Further, it is known that, in the case where the emission layer is formed of a host having a deep HOMO level and a guest having a shallow HOMO level and the guest is sufficiently doped in the emission layer, even when there is a difference in HOMO level between the hole transport layer having a shallow HOMO level and the host, holes to be injected from the hole transport layer are directly injected to the guest. Here, when the quinolino[3,2,1-kl]phenoxazine compound of the present invention is used, for example, as a host for a green phospho- As seen from Table 1, a quinolino[3,2,1-kl]phenoxazine skeleton has a shallower HOMO level. Further, the compound according to the present invention includes two such quinolino[3,2,1-kl]phenoxazine skeletons in the compound. Thus, the compound not only has a further shallower HOMO level but also has an improved hole transporting ability as compared to a compound including one quinolino[3,2,1-kl]phenoxazine skeleton. Accordingly, the compound according to the present invention is a material suitable for a hole transporting material.

On the other hand, the quinolino[3,2,1-kl]phenoxazine skeleton has relatively high molecular planarity. Hence, the presence of a plurality of the skeletons in a compound or an increase in molecular symmetry increases the crystallinity of the compound itself, which makes it difficult to form an amorphous film. Here, when the compound itself has high crystallinity, the solubility of the compound in a solvent lowers, which makes it difficult to purify the compound and also makes it difficult to perform film formation by coating. Further, the sublimation property of the compound also lowers, which makes it difficult to form a film by vapor deposition. As a result, the compound becomes unsuitable for the material for constructing the organic light emitting element. In addition, high crystallinity causes an increase in voltage at which the element is driven and a reduction in life of the element due to the crystallization of the material itself in the production of the element. In view of the foregoing, the quinolino[3,2,1-kl]phenoxazine compound of the present invention not only has an increased solubility but also has reduced intermolecular interaction by allowing an additional alkyl group having 1 to 3 carbon atoms to be possessed by a methylene group for cross-linking phenyl groups in triphenylamine together. Further, the linkage of an oligophenylene group, which links two quinolino[3,2,1-kl]phenoxazine rings together, at a meta position can also suppress the crystallinity of the compound.

As a result, satisfactory film characteristics can be imparted. Further, there is also known a method including linking two quinolino[3,2,1-kl]phenoxazine skeletons together via an oligophenylene group to increase a distance between the skeletons. This method also allows an intramolecular interaction between the quinolino[3,2,1-kl]phenoxazine rings to be reduced. As a result, satisfactory film characteristics can be imparted.

In this regard, however, it is not preferred to adopt a structure like quinolino[3,2,1-de]acridine in which an oxygen atom of quinolino[3,2,1-kl]phenoxazine is replaced by a carbon atom in order to suppress the crystallinity of a molecule. Admittedly, when such structure is adopted, an increase in solubility can be expected because an additional alkyl group is possessed by two methylene groups for cross-linking phenyl groups in triphenylamine together. However, an increase in molecular symmetry also occurs at the same time, with the result that, no large effect of improving the solubility or the like may be provided. Further, quinolino[3,2,1-de]acridine has a deep HOMO level as compared to quinolino[3,2,1-kl]phenoxazine. This is because, although a methylene group or an oxygen atom for cross-linking triphenylamine donates electrons to the amine as described above, the oxygen atom has a larger electron donating ability than the methylene group in a comparison between the methylene group and the oxygen atom. Further, when a compound has many $sp_3$ hybridized carbon atoms, there is fear that the compound is liable to undergo oxidation and has reduced carrier conductivity. Here, it is not preferred to use a material having low carrier conductivity as the material for constructing the organic light emitting element because a voltage at which the element is driven remarkably increases. Further, it is not preferred to use, as a hole transporting material, a material with only one quinolino[3,2,1-kl]phenoxazine ring substituted in order to suppress the crystallinity of a molecule because the HOMO level becomes deeper and the hole transporting ability is also reduced as described above.

The quinolino[3,2,1-kl]phenoxazine compound of the present invention is designed so as to substitute an oligophenylene group having 6 to 18 carbon atoms linked at a meta position to the 11-position or 12-position of quinolino[3,2,1-kl]phenoxazine. When the above-mentioned molecular design is adopted, the extension of conjugation of the compound itself can be suppressed and the $T_1$ energy can be increased. In particular, such a molecular design as to substitute the oligophenylene group having 6 to 18 carbon atoms linked at a meta position to the 12-position of quinolino[3,2,1-kl]phenoxazine can provide additionally high $T_1$ energy. Further, also in the case where quinolino[3,2,1-kl]phenoxazine rings are directly bonded together, the quinolino[3,2,1-kl]phenoxazine rings can be bonded together at the 12-position rather than the 11-position, thereby suppressing the extension of conjugation and increasing the $T_1$ energy. Table 2 below shows $T_1$ energy values of compounds each having two quinolino[3,2,1-kl]phenoxazine rings linked together via a phenylene group. It should be noted that the $T_1$ energy values shown in Table 2 are calculated values obtained by molecular orbital calculation.

TABLE 2

| Structural formula | $T_1$ energy (Calculated value) |
|---|---|
| [structure 1] | 465 nm |
| [structure 2] | 443 nm |
| [structure 3] | 416 nm |

By virtue of the above-mentioned design, the quinolino[3,2,1-kl]phenoxazine compound of the present invention is hard to deteriorate and has high $T_1$ energy and a shallow HOMO level.

Hereinafter, specific examples the quinolino[3,2,1-kl]phenoxazine compound of the present invention are given. In this regard, however, these compounds are merely specific examples, and the present invention is by no means limited thereto.

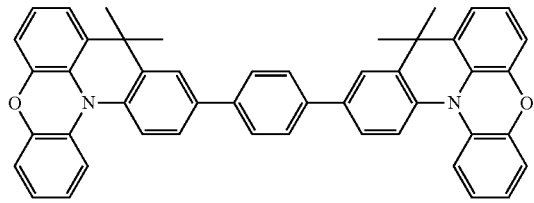 [SMILES: CC1(C)c2cc(-c3ccc(-c4ccc5c(c4)C(C)(C)c4cccc6c4N5c4ccccc4O6)cc3)ccc2N2c3ccccc3Oc3cccc1c32]

A-1

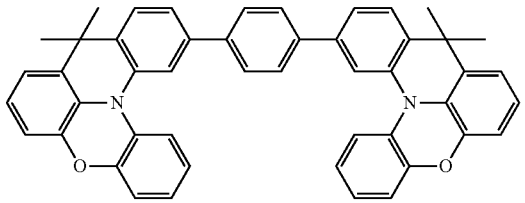

A-2

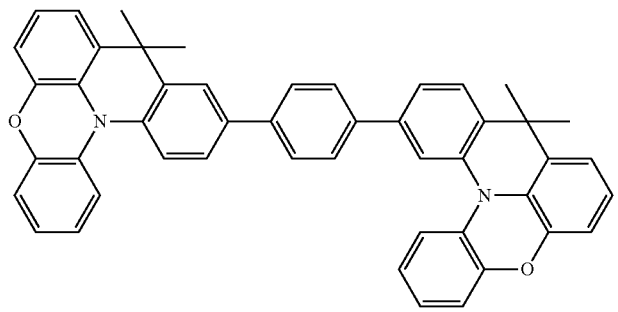

A-3

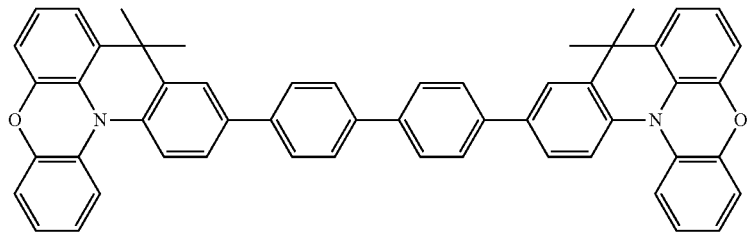

A-4

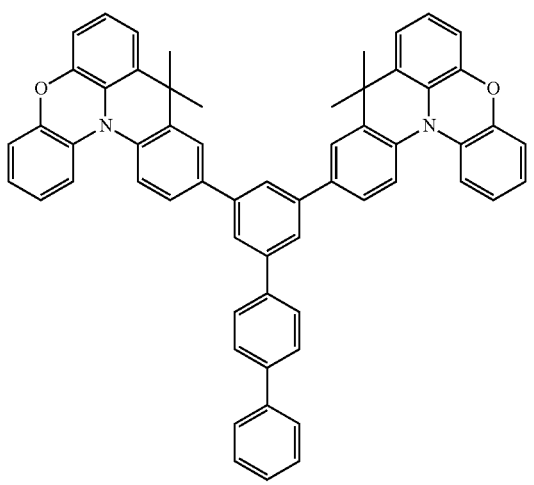

A-5

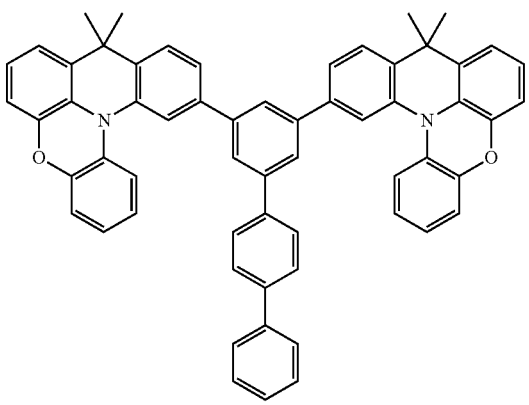

A-6

-continued
A-7
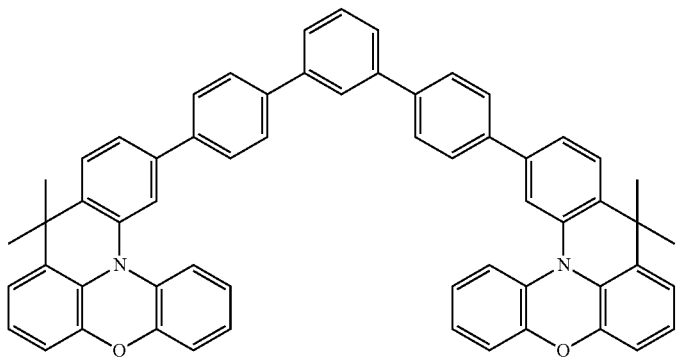
A-8
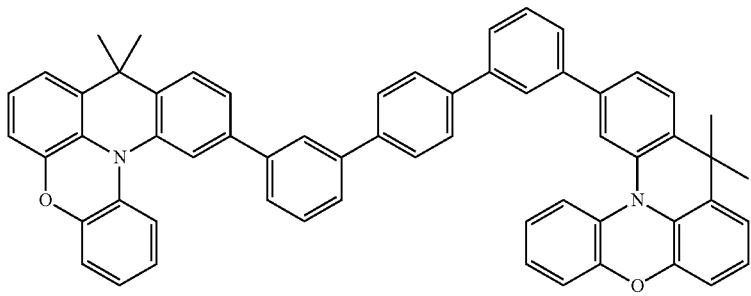
A-9
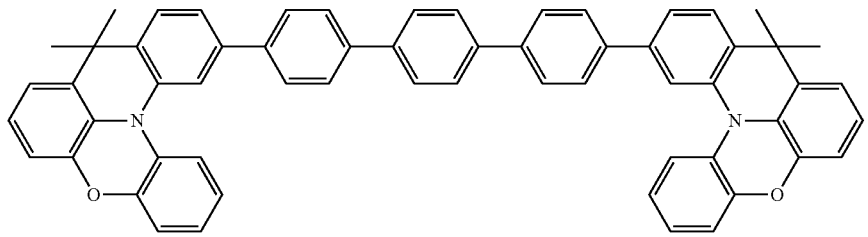
B-1
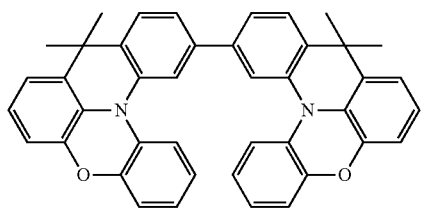
B-2
B-3
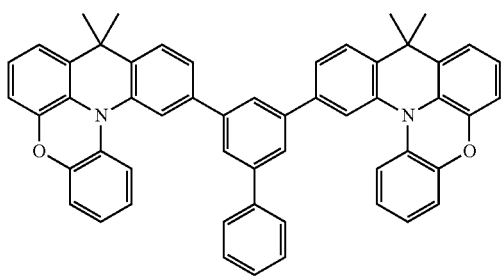
B-4

-continued
B-5
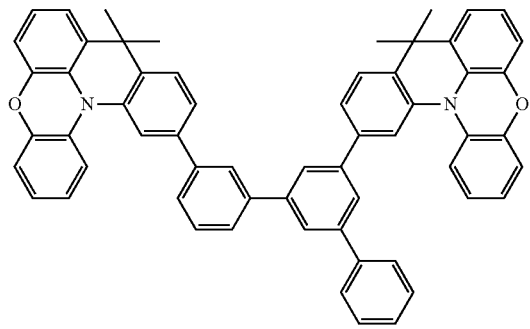
B-6
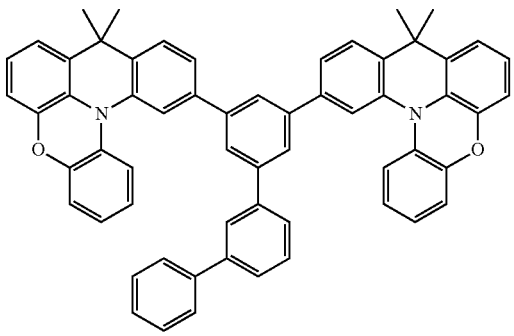
B-7
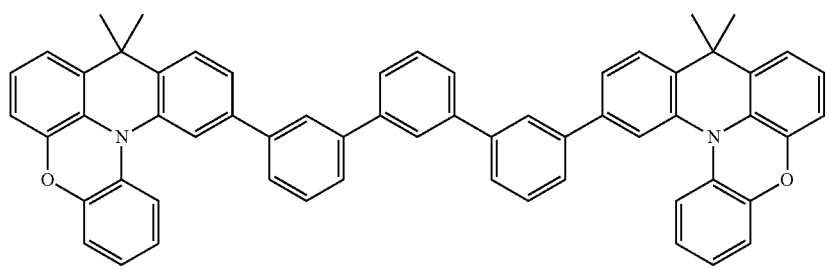
C-1
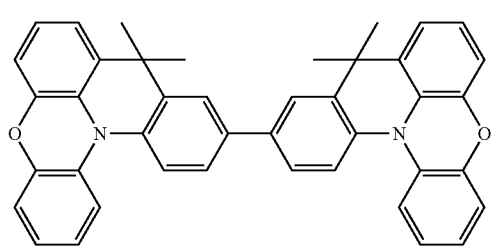
C-2
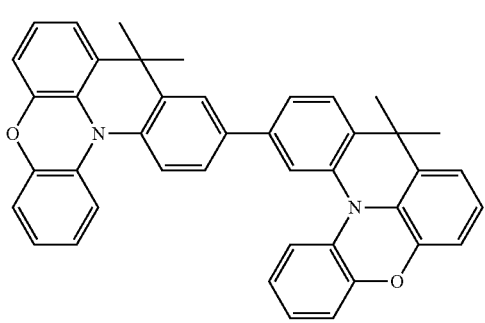
C-3
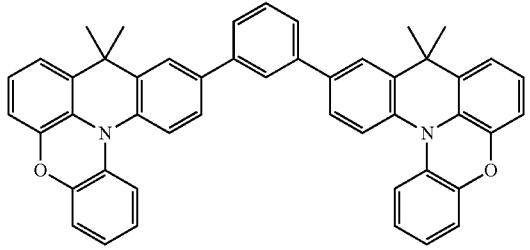 [SMILES: CC1(C)c2cc(-c3cccc(-c4ccc5c(c4)C(C)(C)c4cccc6c4N5c4ccccc4O6)c3)ccc2N2c3ccccc3Oc3cccc1c32]
C-4
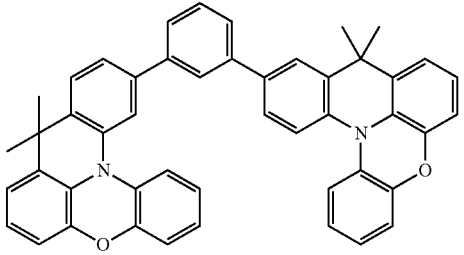
C-5
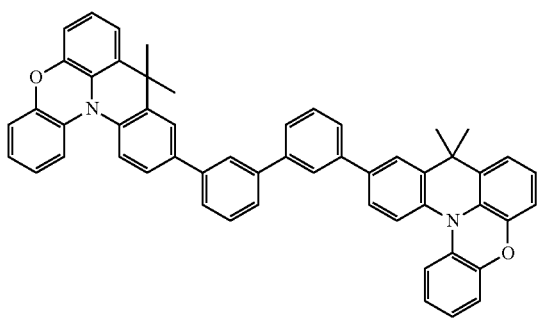
C-6
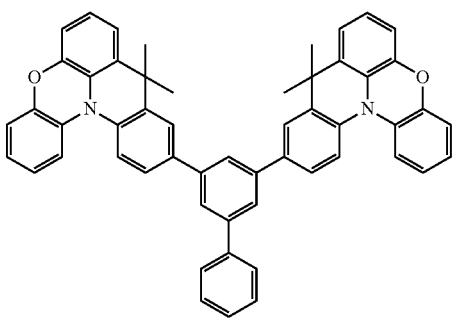

-continued

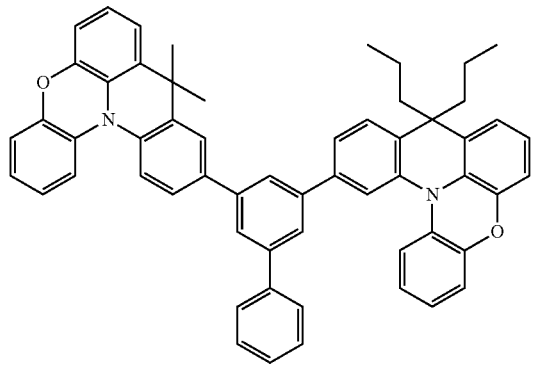
C-7

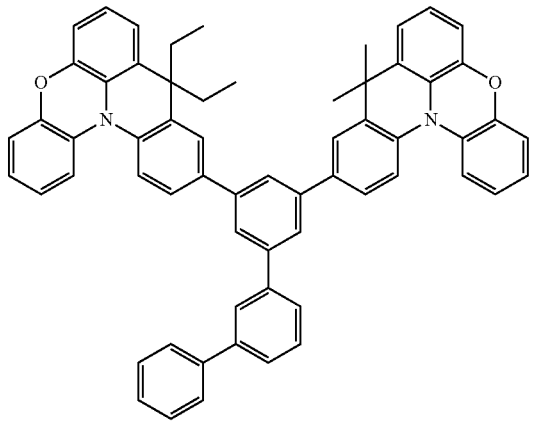
C-8

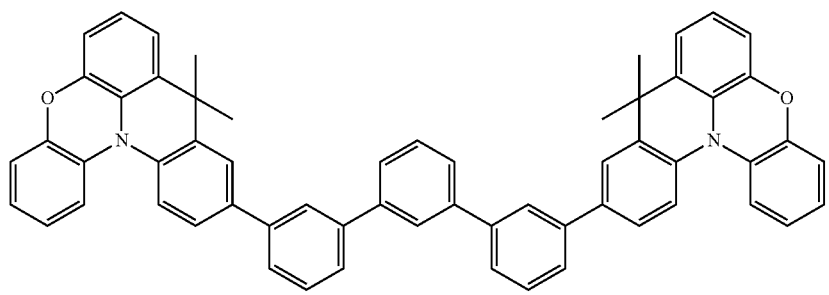
C-9

The compounds belonging to Group A out of the above-mentioned exemplified compounds are a group of compounds in each of which a p-terphenyl skeleton is present in a molecular skeleton through a combination of the oligophenylene group represented by Ar in the formula [1] with the quinolino[3,2,1-kl]phenoxazine skeleton. Each of those compounds belonging to Group A has improved molecular linearity, and hence can be expected to enhance the mobility of carriers and to improve the electrification characteristic of an element. Further, the presence of the p-terphenyl skeleton in the molecular skeleton results in a $T_1$ energy of about 500 nm. Thus, the use of each of the compounds belonging to Group A as a material for constructing a hole transport layer in a green phosphorescent element prevents energy from leaking from an emission layer to the hole transport layer, and hence can be expected to provide an element having higher efficiency.

The compounds belonging to Group B out of the above-mentioned exemplified compounds each have the following feature (B1) or (B2).

(B1) The (carbon atom at the) 12-position of a quinolino [3,2,1-kl]phenoxazine ring has a bond.

(B2) In addition to the above-mentioned feature (B1), benzene rings constructing the oligophenylene group represented by Ar are linked together in a meta orientation.

By virtue of the above-mentioned feature (B1) or (B2), each of those compounds belonging to Group B has higher $T_1$ energy than those of the exemplified compounds belonging to Group C to be described later because the extension of a molecular conjugation length is suppressed. Thus, the use of each of the compounds mainly as a material for a hole transport layer in a blue or green phosphorescent element prevents energy from leaking from an emission layer to the hole transport layer, and hence can be expected to provide an element having higher efficiency. Further, a band gap increases owing to the suppression of the extension of the molecular conjugation length, and the HOMO level becomes deeper along with the increase. Thus, the use is also effective for the case where the amount of holes to be injected to the emission layer is to be suppressed.

The compounds belonging to Group C out of the above-mentioned exemplified compounds each have any one of the following features (C1) and (C2).

(C1) Two quinolino[3,2,1-kl]phenoxazine rings have bonds at the 11 position and the 11 position or the 11 position and the 12 position, respectively.

(C2) In addition to the above-mentioned feature (C1), benzene rings constructing the oligophenylene group represented by Ar are linked together in a meta orientation.

By virtue of the above-mentioned feature (C1) or (C2), those compounds belonging to Group C have intermediate properties of those of Group A and Group B described above. That is, each of the compounds has higher $T_1$ energy than those belonging to Group A because the extension of a molecular conjugation length is suppressed more greatly. Thus, the use of each of the compounds mainly as a material for a hole transport layer in a blue or green phosphorescent element prevents energy from leaking from an emission layer to the hole transport layer, and hence can be expected to provide an element having higher efficiency. Further, a band gap increases owing to the suppression of the extension of the molecular conjugation length, and the HOMO level becomes deeper along with the increase. Thus, the use is also effective for the case where the amount of holes to be injected to the emission layer is to be suppressed. Further, each of the compounds has more improved molecular linearity than those of Group B, and hence can be expected to enhance the mobility of carriers and to improve the electrification characteristic of an element.

Next, the organic light emitting element of the present invention is described. The organic light emitting element of the present invention is a light emitting element including at least a pair of electrodes opposite to each other, i.e., an anode and a cathode, and an organic compound layer disposed between the pair of electrodes. It should be noted that the organic compound layer constructing the organic light emitting element includes an emission layer including a light emitting material. In addition, in the organic light emitting element of the present invention, the quinolino[3,2,1-kl]phenoxazine compound of the present invention is included in the organic compound layer. Further, the organic compound layer preferably includes an emission layer and a hole transport layer adjacent to the emission layer.

As specific aspects of the organic light emitting element of the present invention, there are given the following aspects (i) to (v). In this regard, however, those aspects are merely specific examples of a basic element construction, and the present invention is by no means limited thereto.

(i) (Substrate/)anode/emission layer/cathode
(ii) (Substrate/)anode/hole transport layer/electron transport layer/cathode
(iii) (Substrate/)anode/hole transport layer/emission layer/electron transport layer/cathode
(iv) (Substrate/)anode/hole injection layer/hole transport layer/emission layer/electron transport layer/cathode
(v) (Substrate/)anode/hole transport layer/emission layer/hole-exciton blocking layer/electron transport layer/cathode As aspects other than above-mentioned aspects (i) to (v), for example, there may be adopted a variety of layer constructions as described below. That is, an insulating layer may be provided at an interface between each of electrodes and an organic compound layer, an adhesion layer or an interference layer may be provided, or an electron transport layer or a hole transport layer may be constructed of two layers having different ionization potentials.

In the organic light emitting element of the present invention, an embodiment of the element may be the so-called top emission mode involving extracting light from an electrode on the side opposite to the substrate, or may be the so-called bottom emission mode involving extracting light from the substrate side. Alternatively, there may be adopted a structure in which light is extracted from both surfaces using a substrate and electrodes each formed of a material having light transparency.

In the organic light emitting element of the present invention, the quinolino[3,2,1-kl]phenoxazine compound of the present invention may be used as a material for constructing any one of layers constructing the organic compound layer. Specifically, the compound may be used as a material for constructing any one of a hole injection layer, a hole transport layer, an emission layer, a hole blocking layer, an electron transport layer, and an electron injection layer. It is preferred that the compound be used as a hole injecting/transporting material included in the hole transport layer and the hole injection layer or as a host included in the emission layer.

Here, when the quinolino[3,2,1-kl]phenoxazine compound of the present invention is used as the host included in the emission layer, a phosphorescent light emitting material is preferably used as the guest for the emission layer.

In the organic light emitting element of the present invention, the emission layer may be constructed of multiple kinds of components, and the components may be classified into a main component and a subsidiary component. Here, the main component refers to a compound having the maximum weight ratio out of all compounds for constructing the emission layer, and may be called a host. On the other hand, the subsidiary component refers to a compound other than the main component, and may be called a guest (dopant), an emission assisting material, a charge injecting material, or the like depending on the function of a material. Here, the guest refers to a compound which is responsible for main emission in the emission layer. On the other hand, the host refers to a compound which is present as a matrix around a guest material in the emission layer, and is a compound which is mainly responsible for the transport of carriers and the donation of excitation energy to the guest.

The concentration of the guest with respect to the host is 0.01 wt % or more to 50 wt % or less, preferably 0.1 wt % or more to 20 wt % or less, more preferably 0.1 wt % or more to 10 wt % or less based on the total amount of materials for constructing the emission layer. It should be noted that the concentration of the guest is desirably 10 wt % or less from the viewpoint of preventing concentration quenching. Further, the guest may be uniformly included in the whole layer formed of the host or may be included with a concentration gradient, or a region free of the guest may be provided in a host material layer by partially incorporating the guest in a specific region.

The quinolino[3,2,1-kl]phenoxazine compound of the present invention is mainly used as a material for constructing a hole transport layer in an organic light emitting element having an emission layer in which a phosphorescent light emitting material is used as a guest. In this case, the kind of the phosphorescent light emitting material included in the organic light emitting element is not particularly limited, but a green light emitting material having a maximum emission peak wavelength within the range of 500 nm or more to 530 nm or less is preferred. Alternatively, a blue light emitting material having a maximum emission peak wavelength within the range of 450 nm or more to 470 nm or less is preferred.

In general, in the phosphorescent light emitting element, in order to prevent a reduction in emission efficiency due to nonradiative deactivation from T1 of a host material, the $T_1$ energy of the host material needs to be higher than the $T_1$ energy of the phosphorescent light emitting material as the guest material.

The $T_1$ energy of the quinolino[3,2,1-kl]phenoxazine compound of the present invention is 505 nm or less at lowest in a solution state, which is higher than the $T_1$ energy of a green phosphorescent light emitting material. Further, the $T_1$ energy of the quinolino[3,2,1-kl]phenoxazine compound of the present invention reaches about 440 nm (solution state) at highest. Hence, the compound can provide an organic light emitting element having high emission efficiency even when used as a hole transporting material in a blue phosphorescent light emitting element.

When the quinolino[3,2,1-kl]phenoxazine compound of the present invention is used as a host or a hole injecting/transporting material for an emission layer, a phosphorescent light emitting material to be used as a guest for the emission layer is a metal complex. Specifically, there are given metal complexes such as an iridium complex, a platinum complex, a rhenium complex, a copper complex, a europium complex, and a ruthenium complex. Of those, an iridium complex having strong phosphorescent light emitting property is preferred. Further, for the purpose of assisting the transmission of excitons and carriers, the emission layer may include multiple phosphorescent light emitting materials.

Specific examples of the iridium complex to be used as the phosphorescent light emitting material to be used in the organic light emitting element of the present invention are shown below. In this regard, however, the present invention is by no means limited thereto.
Ir-1
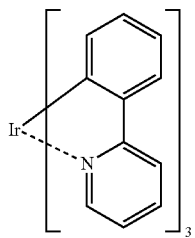
Ir-2
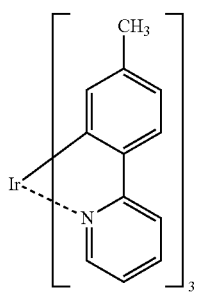
Ir-3
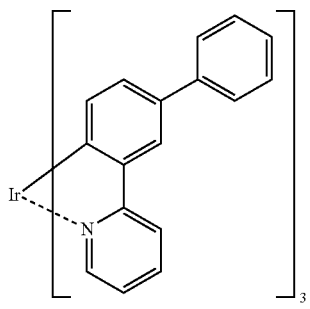
Ir-4
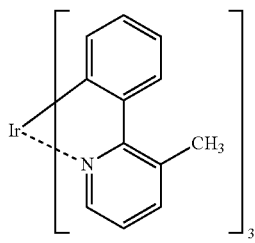
Ir-5
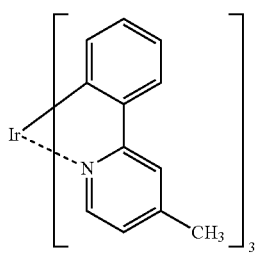
Ir-6
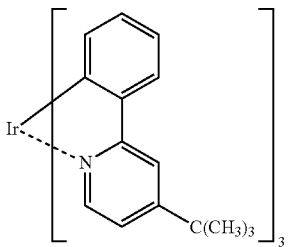
Ir-7
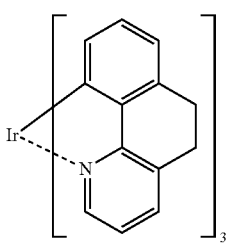
Ir-8
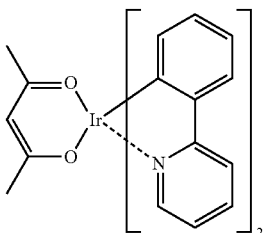
Ir-9
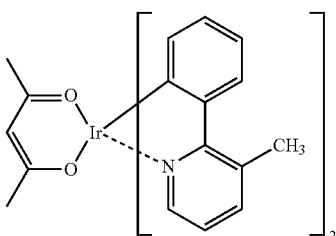
Ir-10
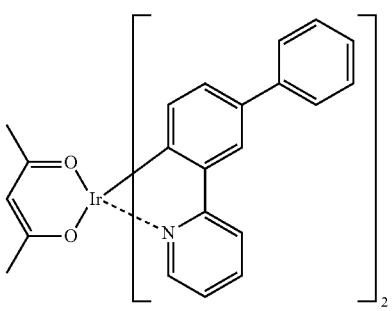
Ir-11
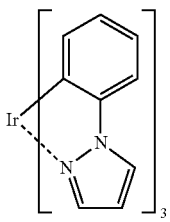

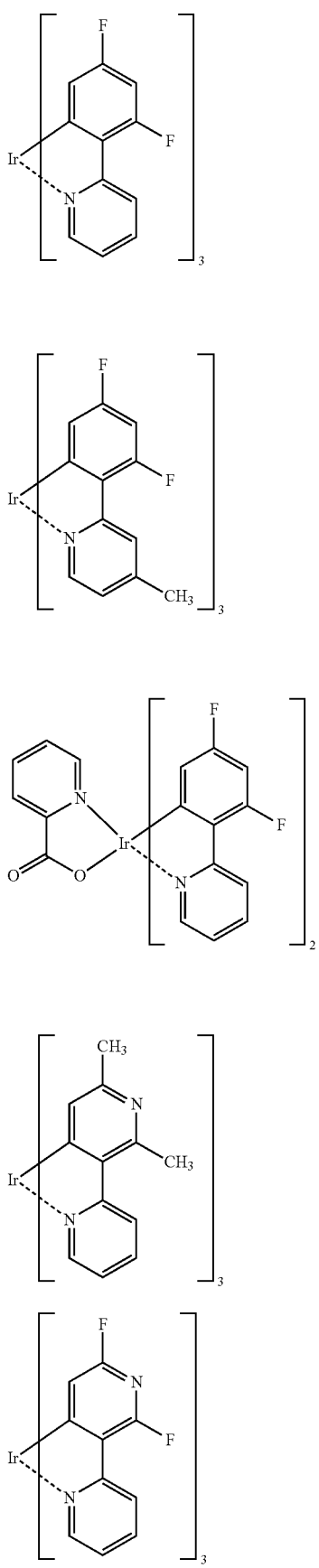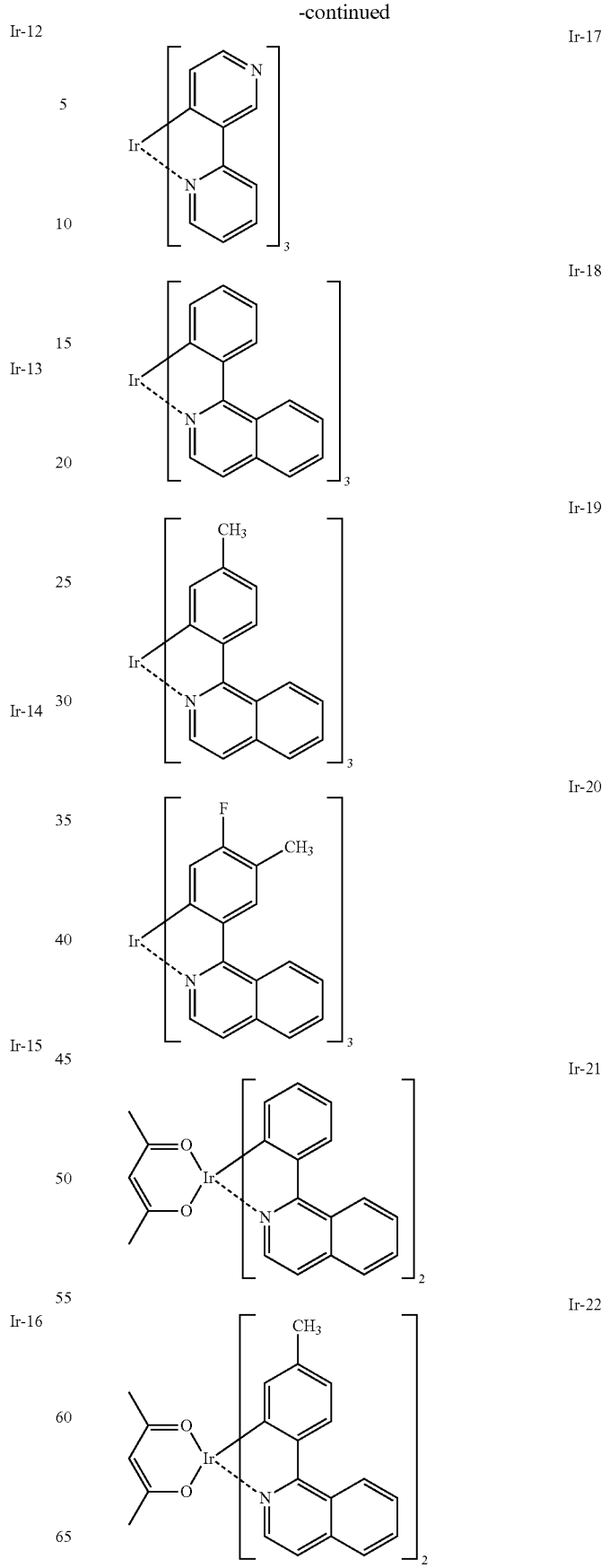

-continued

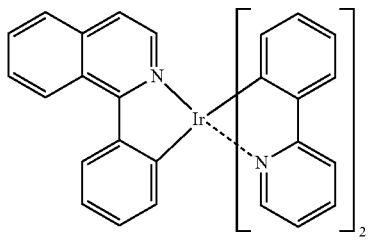
Ir-23

Here, in the organic light emitting element of the present invention, a conventionally known low-molecular or high-molecular compound may be used, as necessary, in addition to the quinolino[3,2,1-kl]phenoxazine compound of the present invention. More specifically, the compound of the present invention may be used in combination with a hole injecting/transporting material, a host, a light emitting material, an electron injecting/transporting material, or the like. Examples of those compounds are given below.

The hole injecting/transporting material is preferably a material having a high hole mobility to facilitate the injection of holes from an anode and to transport the injected holes to an emission layer. Low-molecular and high-molecular materials each having hole injecting/transporting performance are exemplified by a triarylamine derivative, a phenylenediamine derivative, a stilbene derivative, a phthalocyanine derivative, a porphyrin derivative, poly(vinylcarbazole), poly(thiophene), and other conductive polymers.

A light emitting material mainly involved in a light emitting function is exemplified by, in addition to the above-mentioned phosphorescent light emitting guest materials or derivatives thereof, a fused ring compound (for example, a fluorene derivative, a naphthalene derivative, a pyrene derivative, a perylene derivative, a tetracene derivative, an anthracene derivative, or a rubrene), a quinacridone derivative, a coumarin derivative, a stilbene derivative, an organic aluminum complex such as tris(8-quinolinolato)aluminum, an organic beryllium complex, and a polymer derivative such as a poly(phenylenevinylene) derivative, a poly(fluorene) derivative, or a poly(phenylene) derivative.

The electron injecting/transporting material may be optionally selected from materials each of which facilitates the injection of electrons from a cathode and is capable of transporting the injected electrons to an emission layer, and is selected in consideration of, for example, a balance with the hole mobility of the hole injecting/transporting material. A material having electron injecting/transporting performance is exemplified by an oxadiazole derivative, an oxazole derivative, a pyrazine derivative, a triazole derivative, a triazine derivative, a quinoline derivative, a quinoxaline derivative, a phenanthroline derivative, and an organic aluminum complex.

It is recommended that a material for constructing an anode have as large a work function as possible. For example, metal elements such as gold, platinum, silver, copper, nickel, palladium, cobalt, selenium, vanadium, and tungsten, or alloys including combinations thereof, metal oxides such as tin oxide, zinc oxide, indium oxide, indium tin oxide (ITO), and indium zinc oxide may be used. Further, conductive polymers such as polyaniline, polypyrrole, and polythiophene may also be used. One kind of those electrode substances may be used alone, or two or more kinds thereof may be used in combination. Further, the anode may be constructed of a single layer or may be constructed of multiple layers.

Meanwhile, it is recommended that a material for constructing a cathode have a small work function. Examples of the material include alkali metals such as lithium, alkaline earth metals such as calcium, and metal elements such as aluminum, titanium, manganese, silver, lead, and chromium. Alternatively, alloys including combinations of those metal elements may also be used. For example, magnesium-silver, aluminum-lithium, aluminum-magnesium, and the like may be used. Metal oxides such as indium tin oxide (ITO) may also be utilized. One kind of those electrode substances may be used alone, or two or more kinds thereof may be used in combination. Further, the cathode may have a single layer construction or may have a multi-layer construction.

In the organic light emitting element of the present invention, a layer including the quinolino[3,2,1-kl]phenoxazine compound of the present invention and a layer formed of another organic compound are formed by the following method. In general, a thin film is formed by a vacuum vapor deposition method, an ionization vapor deposition method, a sputtering method, or a plasma method. Alternatively, the thin film may be formed by dissolving the compound in an appropriate solvent and subjecting the resultant to a known coating method (for example, a spin coating method, a dipping method, a casting method, an LB method, or an ink jet method). Here, when the layer is formed by a vacuum vapor deposition method, a solution coating method, or the like, the layer is hard to undergo crystallization and the like and is excellent in stability over time. Further, when the film is formed by a coating method, the film may also be formed in combination with an appropriate binder resin.

Examples of the above-mentioned binder resin include, but not limited to, a poly(vinylcarbazole) resin, a polycarbonate resin, a polyester resin, an ABS resin, an acrylic resin, a polyimide resin, a phenolic resin, an epoxy resin, a silicon resin, and a urea resin. Further, one kind of those binder resins may be used alone as a homopolymer or copolymer, or two or more kinds thereof may be used as a mixture. In addition, a known additive such as a plasticizer, an antioxidant, or an ultraviolet absorber may be used in combination, as necessary.

The organic light emitting element according to the present invention may be used for a display device and lighting equipment. In addition, the element may be used for a light source for exposure of an electrophotographic image-forming apparatus, a backlight of a liquid crystal display device, for example.

The display device includes the organic light emitting element according to this embodiment in a display unit. The display unit includes multiple pixels. The pixels each include the organic light emitting element according to this embodiment and a TFT element as one example of a switching element for controlling emission luminance, and an anode or an cathode of the organic light emitting element is connected to a drain electrode or a source electrode of the TFT element. The display device may be used as an image display device such as a PC.

The display device includes an input unit for inputting image information from an area CCD, a linear CCD, a memory card, and the like, and may be an image output device for outputting the input image to a display unit. Further, a display unit included in an image pickup device or an ink jet printer may be provided with both of an image output function, which displays image information input from the outside, and an input function, which serves as an operation panel and inputs processing information for an image. Further, the display device may be used for a display unit of a multifunction printer.

Next, a display device of the present invention is described with reference to the drawings.

FIG. 1 is a cross-sectional schematic diagram illustrating an example of a display device including the organic light emitting element of the present invention and a TFT element as one example of a switching element connected to the organic light emitting element. Two sets of the organic light emitting element and the TFT element are illustrated in a display device 20 of FIG. 1. Details of the structure of the display device are described below.

The display device 20 of FIG. 1 includes a substrate 1 made of glass or the like and a moisture-proof film 2 for protecting a TFT element or an organic compound layer on the substrate. Further, a gate electrode made of metal is represented by reference numeral 3, a gate insulating film is represented by reference numeral 4, and a semiconductor layer is represented by reference numeral 5.

A TFT element 8 includes the semiconductor layer 5, a drain electrode 6, and a source electrode 7. An insulating film 9 is provided above the TFT element 8. An anode 11 of the organic light emitting element is connected to the source electrode 7 via a contact hole 10. The display device is not limited to the above-mentioned construction, and any one of the anode and a cathode has only to be connected to any one of the source electrode and the drain electrode of the TFT element.

In the display device 20 of FIG. 1, an organic compound layer 12 includes multiple organic compound layers but is illustrated like a single layer. A first protective layer 14 and a second protective layer 15 for suppressing the deterioration of the organic light emitting element are provided above a cathode 13.

In the display device 20 of FIG. 1, a switching element is not particularly limited, and a monocrystalline silicon substrate, an MIM element, an a-Si type element, or the like may be used.

Example 1

Synthesis of Exemplified Compound A-1

Exemplified Compound A-1 is a compound which is synthesized through the synthesis of an intermediate TPAOX-PB using phenoxazine as a starting material. A synthesis method therefor is described below with synthesis schemes.

(1) Synthesis of intermediate TPAOX-PB

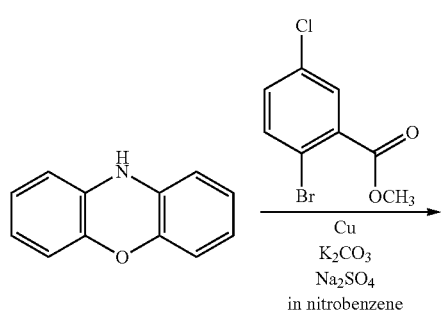

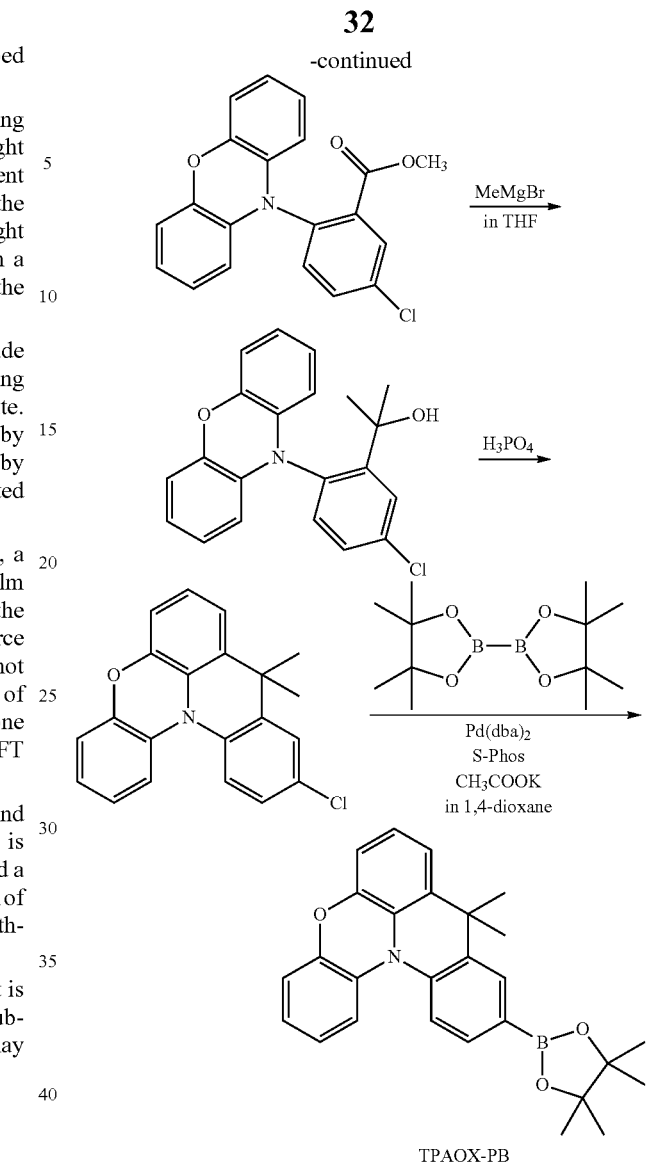

TPAOX-PB

The following reagents and solvent were loaded into a reactor.
10H-Phenoxazine: 10.0 g (54.58 mmol)
Methyl 2-bromo-4-chlorobenzoate: 15.12 g (60.65 mmol)
Copper: 3.85 g (60.65 mmol)
Potassium carbonate: 8.38 g (60.65 mmol)
Sodium sulfate: 8.61 g (60.65 mmol)
Nitrobenzene: 125 ml Next, the reaction solution was stirred with heating under nitrogen at 220° C. for 7 hours. After the completion of the reaction, the reaction solution was concentrated under reduced pressure. To the resultant residue was added ethyl acetate, and the mixture was then washed with an aqueous solution of ammonium chloride. The organic layer was concentrated under reduced pressure to give a crude product. Next, the resultant crude product was purified by column chromatography (silica gel) to afford 15.9 g of methyl 5-chloro-2-(10H-phenoxazin-10-yl)benzoate (yield: 83%).

Subsequently, the following reagent and solvent were loaded into a reactor.
Methyl 5-chloro-2-(10H-phenoxazin-10-yl)benzoate: 15.9 g (45.20 mmol)
Dry tetrahydrofuran: 500 ml Next, to the reaction solution were added dropwise 80 ml (112 mmol) of a 1.4 M solution of methylmagnesium bromide (tetrahydrofuran:toluene=1:3) under nitrogen at an inner temperature of 0° C. The reaction solution was then warmed to room temperature and stirred at the same temperature (room temperature) for 15 hours. After the completion of the reaction, to the reaction solution was added toluene, and the mixture was washed with saturated saline. The organic layer was concentrated under reduced pressure to give a crude product. Next, the resultant crude product was purified by column chromatography (NH gel) to afford 15.0 g of 2-(5-chloro-2-(10H-phenoxazin-10-yl)phenyl)propan-2-ol (yield: 94%).

Subsequently, the following reagent and solvent were loaded into a reactor.
2-(5-Chloro-2-(10H-phenoxazin-10-yl)phenyl)propan-2-ol: 4.0 g (11.37 mmol)
Polyphosphoric acid: 35 ml Next, the reaction solution was stirred with heating under nitrogen at 205° C. for 2 hours. After the completion of the reaction, the reaction solution was left to cool down. Next, to the reaction solution was added toluene, and the mixture was neutralized and washed with an aqueous solution of sodium carbonate. The organic layer was then concentrated under reduced pressure to give a crude product. Next, the resultant crude product was purified by column chromatography (NH gel) to afford 1.08 g of 11-chloro-9,9-dimethyl-9H-quinolino[3,2,1-kl]phenoxazine (yield: 28%).

Subsequently, the following reagents and solvent were loaded into a reactor under a light shielding condition.
11-Chloro-9,9-dimethyl-9H-quinolino[3,2,1-kl]phenoxazine: 0.98 g (2.94 mmol)
Bis(pinacolato)diboron: 0.97 g (3.82 mmol)
Bis(dibenzylideneacetone)palladium(0): 101 mg (0.176 mmol)
2-Dicyclohexylphosphino-2',6'-dimethoxybiphenyl (S-Phos): 145 mg (0.352 mmol)
Potassium acetate: 0.86 g (8.81 mmol)
Dry 1,4-dioxane: 100 ml Next, the reaction solution was stirred with heating under nitrogen at 125° C. for 7 hours. After the completion of the reaction, the reaction solution was left to cool down. Next, to the reaction solution was added toluene, and the mixture was washed with saturated saline. The organic layer was then concentrated to give a crude product. Next, the resultant crude product was purified by column chromatography (silica gel) to afford 1.10 g of PTAOX-PB (yield: 88%).

The resultant compound was identified by $^1$H-NMR analysis.

[$^1$H-NMR (400 MHz, CDCl$_3$)]
δ 7.88 (s, 1H), 7.62-7.59 (m, 2H), 7.31-7.27 (m, 1H), 7.00-6.90 (m, 5H), 6.75-6.73 (d, 1H), 1.90 (s, 3H), 1.35 (s, 12H), 1.22 (s, 3H).

(2) Synthesis of Exemplified Compound A-1

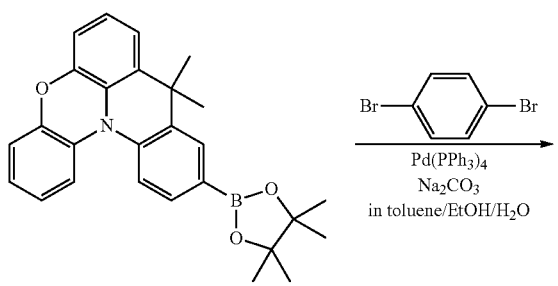

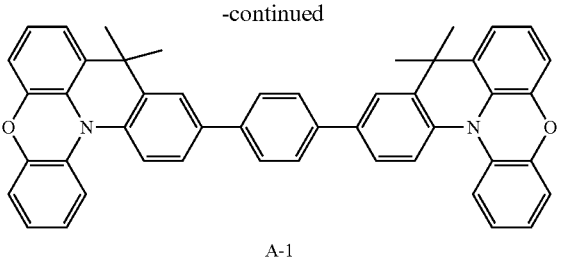

A-1

The following reagents and solvents were loaded into a reactor.
PTAOX-PB: 1.10 g (2.59 mmol)
1,4-Dibromobenzene: 0.265 g (1.12 mmol)
Tetrakis(triphenylphosphine)palladium(0): 130 mg (0.112 mmol)
Toluene: 30 mL
Ethanol: 15 mL
30-wt % aqueous solution of cesium carbonate: 15 mL Next, the reaction solution was deaerated and then stirred with heating under nitrogen at an outer temperature of 80° C. for 7 hours. After the completion of the reaction, the reaction solution was left to cool down. To the reaction solution were then added 200 ml of water. Next, the organic layer was extracted through a separating operation, and the organic layer was then washed with water. The organic layer was then concentrated under reduced pressure to give a crude product. Next, the resultant crude product was purified by column chromatography (silica gel) to afford 610 mg of Exemplified Compound A-1 as a white solid (yield: 81%). Subsequently, the resultant crystal was dried in vacuo at 130° C., and then subjected to sublimation purification under the conditions of 1×10$^{-4}$ Pa and 360° C. to afford 250 mg of Exemplified Compound A-1 with a high purity. The resultant compound was identified. The results are shown below.

[MALDI-TOF-MS]
Observed value: m/z=672.11, calculated value: $C_{48}H_{36}N_2O_2$=672.81

[$^1$H-NMR (400 MHz, CDCl$_3$)]
δ 7.73-7.67 (m, 8H), 7.47-7.45 (d, 2H), 7.37-7.35 (d, 2H), 7.03-6.92 (m, 10H), 6.77-6.75 (d, 2H), 1.93 (s, 6H), 1.29 (s, 6H).

Further, Exemplified Compound A-1 was measured for its T$_1$ energy by the following method.

A toluene dilute solution of Exemplified Compound A-1 was measured for its phosphorescence spectrum at an excitation wavelength of 350 nm under an Ar atmosphere at 77 K. The T$_1$ energy was determined from the peak wavelength of the first emission peak in the resultant phosphorescence spectrum, and found to be 503 nm in terms of a wavelength.

In addition, Exemplified Compound A-1 was measured for its ionization potential by the following method.

Exemplified Compound A-1 was formed into a vapor deposition thin film on a glass substrate by a vacuum vapor deposition method. The vapor deposition thin film was used to measure an ionization potential with a photoelectron spectrometer AC-3 (manufactured by RIKEN KEIKI CO., LTD.). As a result of the measurement, Exemplified Compound A-1 had an ionization potential of 5.53 eV.

Example 2

Synthesis of Exemplified Compound C-3

210 mg of Exemplified Compound C-3 were obtained as a white solid by the same synthesis as that in Example 1 except that 1,3-dibromobenzene was used in place of 1,4-dibromobenzene in Example 1(2).

A toluene dilute solution of Exemplified Compound C-3 was measured for its phosphorescence spectrum at an excitation wavelength of 350 nm under an Ar atmosphere at 77 K. The $T_1$ energy was determined from the peak wavelength of the first emission peak of the resultant phosphorescence spectrum, and found to be 483 nm in terms of a wavelength.

Example 3

In this example, a bottom emission type organic light emitting element having the construction of "anode/hole transport layer/emission layer/hole blocking layer/electron transport layer/cathode" successively provided on a substrate was produced by the following method. Some of materials used in this example are shown below.

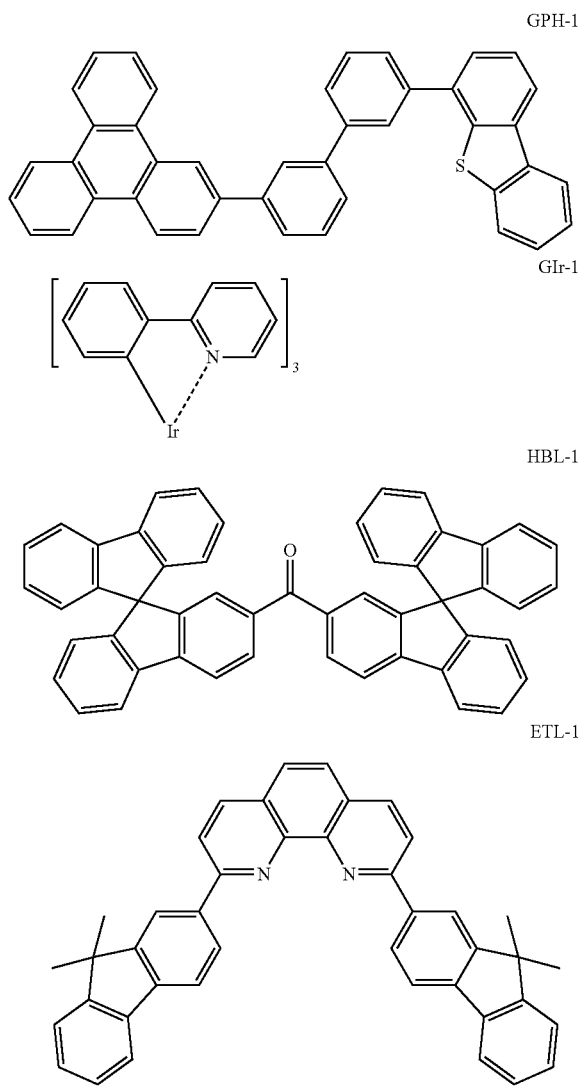

It should be noted that GPH-1 used in this example was synthesized with reference to International Publication WO2009/021126.

Further, GIr-1 used in this example was synthesized with reference to A New Synthetic Route to the Preparation of a Series of Strong Photoreducing Agents: fac Tris-Ortho-Metalated Complexes of Iridium (III) with Substituted 2-Phenylpyridines. (K. Dedeian et al., Inorganic Chemistry, Vol. 30, No. 8, p. 1685 (1991)).

Further, HBL-1 used in this example was synthesized with reference to International Publication WO2004/093207.

Further, ETL-1 used in this example was synthesized with reference to International Publication WO2009/139501.

Next, a manufacturing method for the organic light emitting element is described. First, indium zinc oxide (IZO) was formed into a film to serve as an anode on a glass substrate by a sputtering method. In this case, the thickness of the anode was set to 120 nm. The substrate having formed thereon the anode as described above was used as a transparent conductive supporting substrate (IZO substrate) in the following steps. Next, organic compound layers and electrode layers shown in Table 3 below were continuously formed as films on the anode by vacuum vapor deposition through resistance heating in a vacuum chamber at $1\times10^{-5}$ Pa. In this case, an opposite electrode (cathode) was produced so as to have an area of 3 $mm^2$.

TABLE 3

| | Material | Thickness [nm] |
|---|---|---|
| Hole transport layer | Exemplified Compound A-1 | 40 |
| Emission layer | Host: GPH-1 Guest: GIr-1 (host:guest = 90:10 (weight ratio)) | 30 |
| Hole blocking layer | HBL-1 | 10 |
| Electron transport layer | ETL-1 | 30 |
| First metal electrode layer (cathode) | LiF | 0.5 |
| Second metal electrode layer (cathode) | Al | 100 |

Next, the resultant was covered with a protective glass sheet and sealed with an acrylic resin-based adhesive under a dry air atmosphere in order that an organic light emitting element did not undergo element deterioration due to moisture adsorption. Thus, an organic light emitting element was obtained.

A voltage of 4.5 V was applied to the resultant organic light emitting element while the ITO electrode was used as a positive electrode and the Al electrode was used as a negative electrode. As a result, the element was observed to emit green light having an emission efficiency of 47 cd/A, a luminance of 2,500 $cd/m^2$, and CIE chromaticity coordinates of (x, y)= (0.32, 0.62). In addition, the light emitting element showed a luminance half-life of 85 hours at a constant current density of 100 $mA/cm^2$. It should be noted that, regarding characteristics of the organic light emitting element, a current-voltage characteristic was measured with an ammeter 2700 manufactured by Keithley Instruments Inc. and an emission luminance was measured with a BM7-fast manufactured by TOPCON CORPORATION.

Example 4

An element was produced by the same method as in Example 3 except that Exemplified Compound A-2 was used in place of Exemplified Compound A-1 as the material for the hole transport layer in Example 3. Further, the resultant element was evaluated by the same method as in Example 3. Table 4 shows the results.

Example 5

An element was produced by the same method as in Example 3 except that Exemplified Compound C-1 was used in place of Exemplified Compound A-1 as the material for the hole transport layer in Example 3. Further, the resultant element was evaluated by the same method as in Example 3. Table 4 shows the results.

Example 6

An element was produced by the same method as in Example 3 except that Exemplified Compound C-3 was used in place of Exemplified Compound A-1 as the material for the hole transport layer in Example 3. Further, the resultant element was evaluated by the same method as in Example 3. Table 4 shows the results.

Example 7

An element was produced by the same method as in Example 3 except that Compound GIr-2 below was used in place of Compound GIr-1 as the guest for the emission layer in Example 3. Further, the resultant element was evaluated by the same method as in Example 3. Table 4 shows the results.

GIr-2

Example 8

An element was produced by the same method as in Example 3 except that Compound HBL-2 below was used in place of Compound HBL-1 as the material for the hole blocking layer in Example 3. Further, the resultant element was evaluated by the same method as in Example 3. Table 4 shows the results.

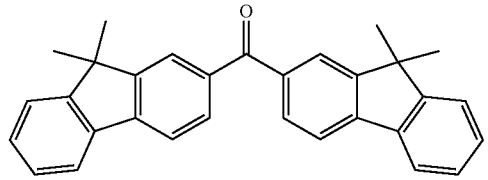

HBL-2

Comparative Example 1

An element was produced by the same method as in Example 3 except that Comparative Compound GH-01 below was used in place of Exemplified Compound A-1 as the material for the hole transport layer in Example 3. Further, the resultant element was evaluated by the same method as in Example 3. Table 4 shows the results.

GH-01

Comparative Example 2

An element was produced by the same method as in Example 3 except that Comparative Compound AH-01 below was used in place of Exemplified Compound A-1 as the material for the hole transport layer in Example 3. Further, the resultant element was evaluated in the same manner as in Example 3. Table 4 shows the results.

TABLE 4

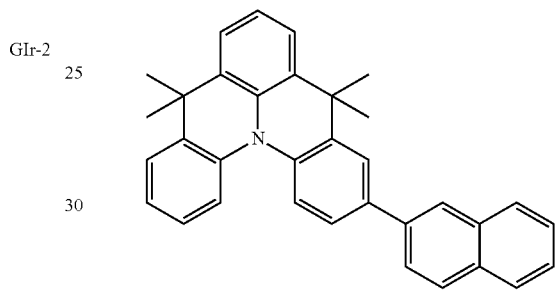

AH-01

| | Hole transport layer | Guest | Hole blocking layer | CIE chromaticity coordinates | Applied voltage [V] | Emission efficiency [cd/A] | Luminance half-life at 100 mA·cm² [hr] |
|---|---|---|---|---|---|---|---|
| Example 3 | A-1 | GIr-1 | HBL-1 | (0.32, 0.62) | 4.5 | 47 | 85 |
| Example 4 | A-2 | GIr-1 | HBL-1 | (0.33, 0.62) | 4.7 | 45 | 79 |
| Example 5 | C-1 | GIr-1 | HBL-1 | (0.32, 0.63) | 5.2 | 50 | 64 |
| Example 6 | C-3 | GIr-1 | HBL-1 | (0.33, 0.64) | 5.3 | 44 | 68 |
| Example 7 | A-1 | GIr-2 | HBL-1 | (0.31, 0.61) | 5.5 | 42 | 62 |
| Example 8 | A-1 | GIr-1 | HBL-2 | (0.32, 0.62) | 5.8 | 39 | 59 |

TABLE 4-continued

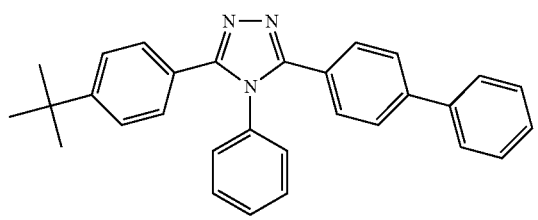

AH-01

| | Hole transport layer | Guest | Hole blocking layer | CIE chromaticity coordinates | Applied voltage [V] | Emission efficiency [cd/A] | Luminance half-life at 100 mA·cm² [hr] |
|---|---|---|---|---|---|---|---|
| Comparative Example 1 | GH-01 | GIr-1 | HBL-1 | (0.27, 0.50) | 5.3 | 28 | 21 |
| Comparative Example 2 | AH-01 | GIr-1 | HBL-1 | (0.32, 0.62) | 6.1 | 44 | 35 |

Example 9

In this example, a bottom emission type organic light emitting element having the construction of "anode/hole transport layer/emission layer/hole blocking layer/electron transport layer/cathode" successively provided on a substrate was produced by the following method. Some of materials used in this example are shown below.

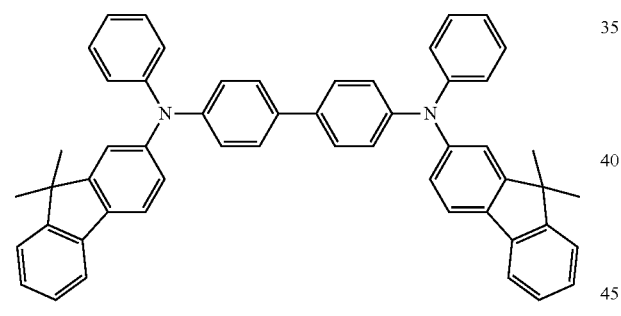

HIL-1

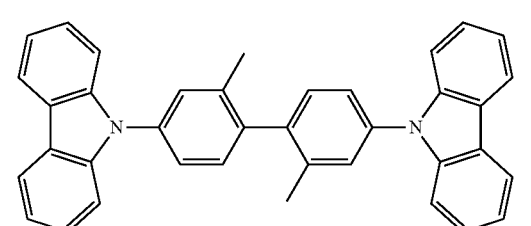

BPH-1

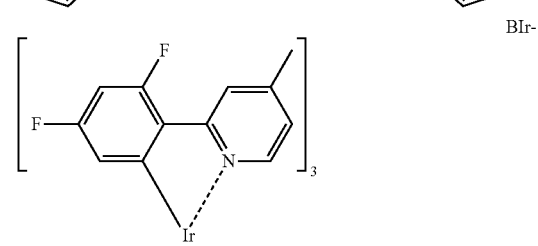

BIr-1

-continued

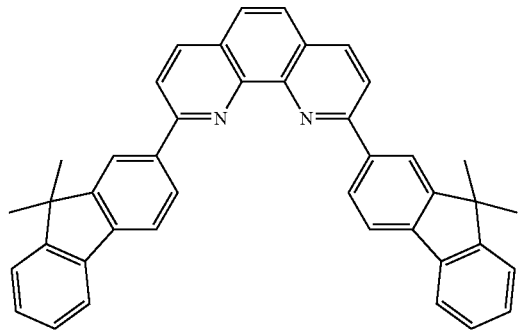

HBL-2

ETL-1

It should be noted that HIL-1 and ETL-1 used in this example were synthesized with reference to International Publication WO2009/139501.

Further, BPH-1 used in this example was synthesized with reference to Confinement of triplet energy on phosphorescent molecules for highly-efficient organic blue-light-emitting devices. (S. Tokito et al., Applied Physics Letters, Vol. 83, No. 3, p. 569 (2003)).

Further, BIr-1 used in this example was synthesized with reference to US Patent Application Publication No. 2007/0232803.

Further, HBL-2 used in this example was a commercially available product (manufactured by Aldrich) subjected to sublimation purification before use.

Next, a manufacturing method for the organic light emitting element is described. First, indium zinc oxide (IZO) was formed into a film to serve as an anode on a glass substrate by a sputtering method. In this case, the thickness of the anode was set to 120 nm. The substrate having formed thereon the anode (IZO electrode) as described above was used as a transparent conductive supporting substrate (IZO substrate) in the following steps. Next, organic compound layers and electrode layers shown in Table 5 below were continuously formed as films on the anode by vacuum vapor deposition through resistance heating in a vacuum chamber at $1\times10^{-5}$ Pa. In this case, an opposite electrode was produced so as to have an area of 3 mm².

TABLE 5

|  | Material | Thickness [nm] |
|---|---|---|
| Hole injection layer | HIL-1 | 10 |
| Hole transport layer | Exemplified Compound B-2 | 30 |
| Emission layer | Host: BPH-1 Guest: BIr-1 (host:guest = 90:10 (weight ratio)) | 30 |
| Hole blocking layer | HBL-2 | 10 |
| Electron transport layer | ETL-1 | 30 |
| First metal electrode layer (cathode) | LiF | 0.5 |
| Second metal electrode layer (cathode) | Al | 100 |

Next, the resultant was covered with a protective glass sheet and sealed with an acrylic resin-based adhesive under a dry air atmosphere so that an organic light emitting element did not undergo element deterioration due to moisture adsorption. Thus, an organic light emitting element was obtained.

A voltage of 6.5 V was applied to the resultant organic light emitting element while the ITO electrode was used as a positive electrode and the Al electrode was used as a negative electrode. As a result, the element was observed to emit blue light having an emission efficiency of 8.6 cd/A and CIE chromaticity coordinates of (x, y)=(0.15, 0.33). In addition, the light emitting element showed a luminance half-life of 125 hours at a constant current density of 4 mA/cm². Regarding characteristics of the organic light emitting element, a current-voltage characteristic was measured with an ammeter 2700 manufactured by Keithley Instruments Inc. and an emission luminance was measured with a BM7-fast manufactured by TOPCON CORPORATION.

Example 10

An element was produced by the same method as in Example 9 except that Exemplified Compound B-1 was used in place of Exemplified Compound B-2 as the material for the hole transport layer in Example 9. Further, the resultant element was evaluated by the same method as in Example 9. Table 4 shows the results.

Example 11

An element was produced by the same method as in Example 9 except that Compound BIr-2 below was used in place of Compound BIr-1 as the guest for the emission layer in Example 9. Further, the resultant element was evaluated by the same method as in Example 9. Table 4 shows the results.

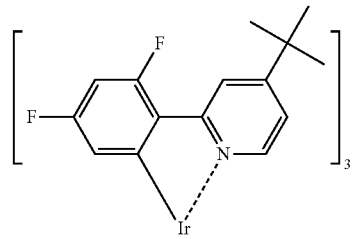

BIr-2

Example 12

An element was produced by the same method as in Example 9 except that Compound HIL-2 below was used in place of Compound HIL-1 as the material for the hole transport layer in Example 9. Further, the resultant element was evaluated by the same method as in Example 9. Table 4 shows the results.

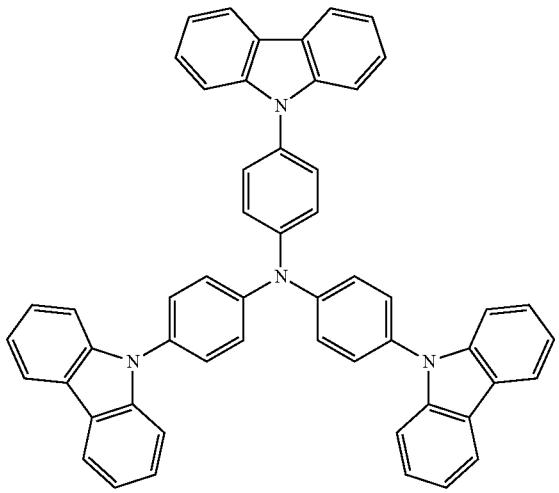

HIL-2

Comparative Example 3

An element was produced by the same method as in Example 9 except that Comparative Compound GH-01 below was used in place of Exemplified Compound B-2 as the material for the hole transport layer in Example 9. Further, the resultant element was evaluated by the same method as in Example 9. Table 4 shows the results.

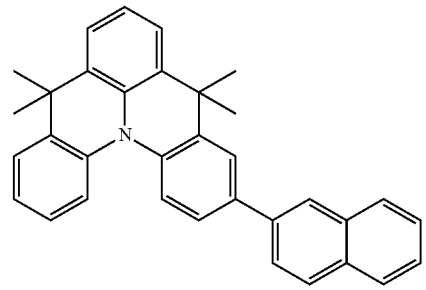

GH-01

Comparative Example 4

An element was produced by the same method as in Example 9 except that Comparative Compound AH-02 below was used in place of Exemplified Compound B-2 as the material for the hole transport layer in Example 9. Further, the resultant element was evaluated in the same manner as in Example 9. Table 4 shows the results.

TABLE 6

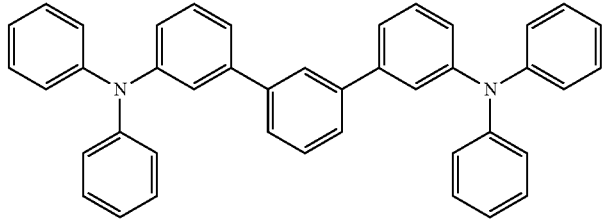 [SMILES: c1ccc(N(c2ccccc2)c2cccc(-c3cccc(-c4cccc(N(c5ccccc5)c5ccccc5)c4)c3)c2)cc1]

AH-02

| | Hole transport layer | Guest | Hole injection layer | CIE chromaticity coordinates | Applied voltage [V] | Emission efficiency [cd/A] | Luminance half-life at 100 mA·cm$^2$ [hr] |
|---|---|---|---|---|---|---|---|
| Example 9 | B-2 | BIr-1 | HIL-1 | (0.15, 0.33) | 5.2 | 15 | 96 |
| Example 10 | B-1 | BIr-1 | HIL-1 | (0.16, 0.34) | 5.1 | 17 | 113 |
| Example 11 | B-2 | BIr-2 | HIL-1 | (0.16, 0.30) | 5.6 | 13 | 102 |
| Example 12 | B-2 | BIr-1 | HIL-2 | (0.16, 0.33) | 6.2 | 14 | 87 |
| Comparative Example 3 | GH-01 | BIr-1 | HIL-1 | (0.19, 0.45) | 5.3 | 6 | 48 |
| Comparative Example 4 | AH-02 | BIr-1 | HIL-1 | (0.16, 0.33) | 6.1 | 13 | 59 |

As described above, the quinolino[3,2,1-kl]phenoxazine compound of the present invention is a novel compound which is hard to deteriorate and has high $T_1$ energy and a deep HOMO level. Accordingly, the use of the quinolino[3,2,1-kl]phenoxazine compound of the present invention as a material for constructing an organic light emitting element can provide a light emitting element having a low drive volatage, high emission efficiency, and good durability.

REFERENCE SIGNS LIST 1 substrate
2 moisture-proof film
3 gate electrode
4 gate insulating film
5 semiconductor layer
6 drain electrode
7 source electrode
8 TFT element
9 insulating film
10 contact hole
11 anode
12 organic compound layer
13 cathode
14 first protective layer
15 second protective layer
20 display device While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-268480, filed Dec. 1, 2010, which is hereby incorporated by reference herein in its entirety.

The invention claimed is:

1. A quinolino[3,2,1-kl]phenoxazine compound represented by the following general formula [1]:

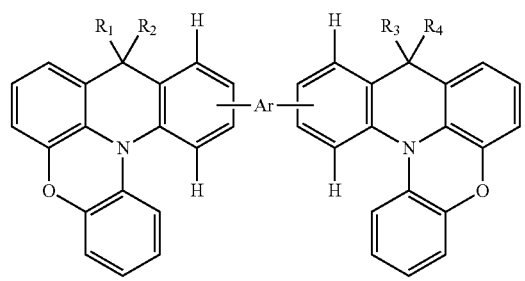

[1]

where $R_1$ to $R_4$ each independently represent a hydrogen atom or an alkyl group having 1 to 3 carbon atoms, Ar represents a single bond or an oligophenylene group having 6 to 18 carbon atoms, and Ar is bonded to quinolino[3,2,1-kl]phenoxazine at 11-position or 12-position.

2. A quinolino[3,2,1-kl]phenoxazine compound represented by the following general formula [2]:

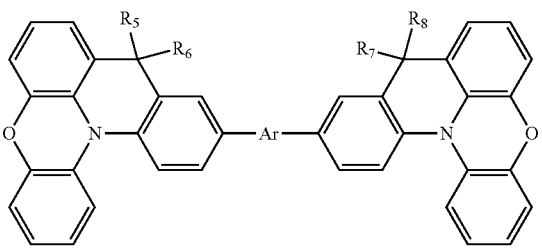

[2]

where $R_5$ to $R_8$ each independently represent a hydrogen atom or an alkyl group having 1 to 3 carbon atoms, Ar is bonded to quinolino[3,2,1-kl]phenoxazine at 11-position, and Ar represents a single bond or an oligophenylene group having 6 to 18 carbon atoms represented by the following general formula [3]:

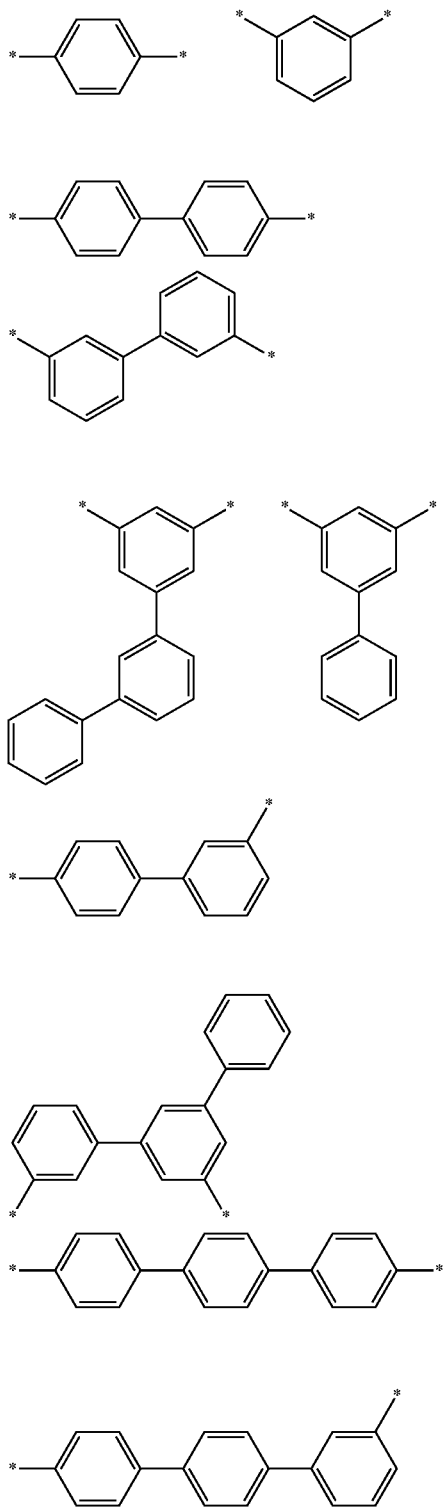

[3]

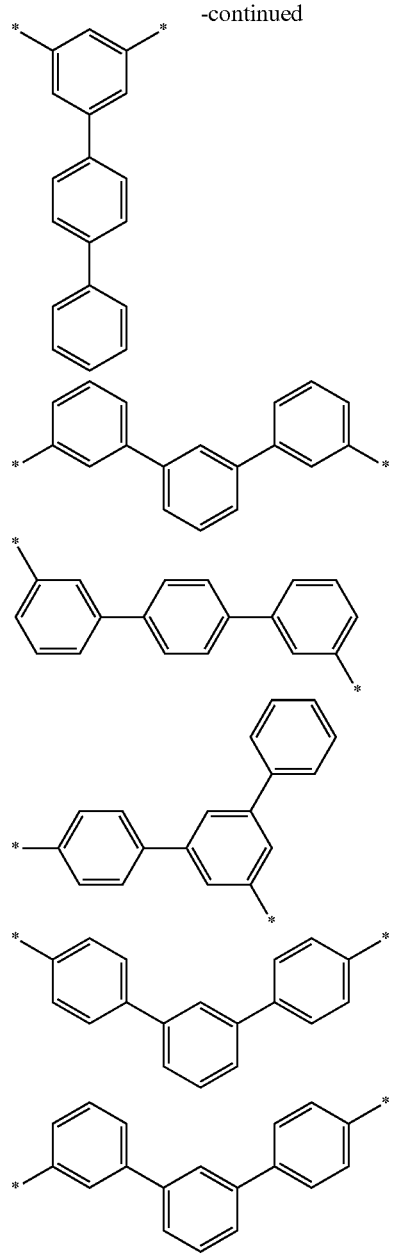

-continued where * represents a position at which the oligophenylene group is bonded to quinolino[3,2,1-kl]phenoxazine in the formula [2].

3. An organic light emitting element comprising:
an anode;
a cathode; and
an organic compound layer disposed between the anode and the cathode,
wherein the organic compound layer comprises the quinolino[3,2,1-kl]phenoxazine compound according to claim 1.

4. The organic light emitting element according to claim 3, wherein the organic compound layer comprises an emission layer and a hole transport layer adjacent to the emission layer; and
wherein the hole transport layer comprises the quinolino [3,2,1-kl]phenoxazine compound.

5. The organic light emitting element according to claim 4, wherein the emission layer comprises a host and a guest;

wherein the host comprises the quinolino[3,2,1-kl]phenoxazine compound; and wherein the guest comprises a phosphorescent light emitting material.

6. The organic light emitting element according to claim 5, wherein the phosphorescent light emitting material comprises an iridium complex.

7. A display device comprising multiple pixels, wherein the pixels each comprise the organic light emitting element according to claim 3 and a switching element connected to the organic light emitting element.

8. An image input device comprising the display device according to claim 7.

9. A lighting equipment comprising the organic light emitting element according to claim 3.

10. The organic light-emitting device according to claim 3, wherein the organic compound layer comprises an emission layer;

wherein the emission layer comprises a host and a guest; and wherein the host is the quinolino[3,2,1-kl]phenoxazine compound.

11. The organic light-emitting device according to claim 4, wherein the emission layer comprises a host and a guest; and wherein the guest comprises an iridium complex.

12. The quinolino[3,2,1-kl]phenoxazine compound according to claim 1, wherein the Ar denotes the oligophenylene group; and wherein the Ar is bound to quinolino[3,2,1-kl]phenoxazine compound at a meta position.

* * * * *